United States Patent
Jin et al.

(10) Patent No.: US 9,907,876 B2
(45) Date of Patent: Mar. 6, 2018

(54) SWITCHABLE GAS AND LIQUID RELEASE AND DELIVERY DEVICES, SYSTEMS, AND METHODS

(71) Applicants: The Regents of the University of California, Oakland, CA (US); Sensable Technologies LLC, San Diego, CA (US)

(72) Inventors: Sungho Jin, San Diego, CA (US); Calvin Gardner, La Jolla, CA (US); Stewart Matthew, London (GB)

(73) Assignees: The Regents of the University of California, Oakland, CA (US); Sensable Technologies LLC, New York, NY (US)

( * ) Notice: Subject to any disclaimer, the term of this patent is extended or adjusted under 35 U.S.C. 154(b) by 182 days.

(21) Appl. No.: 14/786,505

(22) PCT Filed: Apr. 22, 2014

(86) PCT No.: PCT/US2014/035054
§ 371 (c)(1),
(2) Date: Oct. 22, 2015

(87) PCT Pub. No.: WO2014/176291
PCT Pub. Date: Oct. 30, 2014

(65) Prior Publication Data
US 2016/0067367 A1    Mar. 10, 2016

Related U.S. Application Data

(60) Provisional application No. 61/814,810, filed on Apr. 22, 2013.

(51) Int. Cl.
*A61L 9/00* (2006.01)
*B05B 9/03* (2006.01)
(Continued)

(52) U.S. Cl.
CPC .............. *A61L 9/12* (2013.01); *A61L 9/04* (2013.01); *A61L 9/042* (2013.01); *A61L 9/122* (2013.01);
(Continued)

(58) Field of Classification Search
CPC ............. A61L 9/12; A61L 9/127; A61L 9/122
(Continued)

(56) References Cited

U.S. PATENT DOCUMENTS 5,610,674 A    3/1997   Martin
5,887,118 A    3/1999   Huffman et al.
(Continued)

FOREIGN PATENT DOCUMENTS

CN    202650995 U    1/2013
EP    1846044 A1    10/2007
WO    2013012442 A1    1/2013

OTHER PUBLICATIONS

Cater, J.P., "Approximating the Senses," IEEE International Conference on Systems, Man, and Cybernetics, 1994, 1781.
(Continued)

*Primary Examiner* — Kevin Joyner
(74) *Attorney, Agent, or Firm* — Perkins Coie LLP

(57) ABSTRACT

Methods, systems, and devices are disclosed for implementing switchable dispensing and/or delivery of scented substances. In one aspect, a device includes a cartridge structured to include one or more chambers containing one or more scented substances contained in a corresponding chamber, a housing structured to include a compartment to hold the cartridge, an opening to allow the scented substances to dispense to an outer environment from the device, and one or more transporting channels formed between the compartment and the opening, in which each of the one or more transporting channels is configured to accelerate a scented substance from the corresponding chamber to the (Continued)

opening, and an actuator switch arranged in a corresponding transporting channel and operable to move between an open position and a closed position based on an applied signal to selectively allow passage of the scented substance from the corresponding transporting path.

39 Claims, 29 Drawing Sheets

(51) Int. Cl.

| | | |
|---|---|---|
| *A61L 9/04* | (2006.01) | |
| *A61L 9/12* | (2006.01) | |
| *B05B 12/02* | (2006.01) | |
| *B05B 12/14* | (2006.01) | |
| *A61L 9/03* | (2006.01) | |
| *G02C 11/00* | (2006.01) | |

(52) U.S. Cl.
CPC .............. *A61L 9/125* (2013.01); *A61L 9/127* (2013.01); *B05B 12/02* (2013.01); *B05B 12/14* (2013.01); *A61L 9/037* (2013.01); *A61L 2209/133* (2013.01); *A61L 2209/15* (2013.01); *G02C 11/00* (2013.01)

(58) Field of Classification Search
USPC ........................................ 422/4; 239/302, 34
See application file for complete search history.

(56) References Cited

U.S. PATENT DOCUMENTS

| | | | |
|---|---|---|---|
| 5,972,290 | A | 10/1999 | De Sousa |
| 6,025,902 | A | 2/2000 | Wittek |
| 6,135,431 | A | 10/2000 | Muhmel et al. |
| 6,244,894 | B1 | 6/2001 | Miyashita |
| 6,325,475 | B1 | 12/2001 | Hayes et al. |
| 6,338,818 | B2 | 1/2002 | Budman |
| 6,371,165 | B1 | 4/2002 | Manne |
| 6,713,024 | B1 | 3/2004 | Arnell et al. |
| 6,783,084 | B1 | 8/2004 | Nelson |
| 6,842,218 | B1 | 1/2005 | Manne |
| 7,152,758 | B2 | 12/2006 | Fazzio et al. |
| 7,154,579 | B2 | 12/2006 | Selander et al. |
| 7,200,363 | B2 | 4/2007 | Greco et al. |
| 7,203,417 | B2 | 4/2007 | Manne |
| 7,376,344 | B2 | 5/2008 | Manne |
| 7,437,061 | B2 | 10/2008 | Manne |
| 7,601,297 | B2 | 10/2009 | Gygax et al. |
| 7,622,084 | B2 | 11/2009 | Cho et al. |
| 8,032,014 | B2 | 10/2011 | Cheung |
| 8,050,545 | B2 | 11/2011 | Manne |
| 8,052,934 | B2 | 11/2011 | Manne |
| 8,068,725 | B2 | 11/2011 | Cheung |
| 8,090,244 | B2 | 1/2012 | Belongia et al. |
| 8,100,348 | B2 * | 1/2012 | Wissink ............... B01F 3/0807 239/310 |
| 8,238,970 | B2 | 8/2012 | Seo et al. |
| 2002/0114744 | A1 | 8/2002 | Chiao et al. |
| 2003/0223040 | A1 | 12/2003 | Schermerhorn |
| 2004/0037764 | A1 * | 2/2004 | Gau ........................ A61L 9/035 422/305 |
| 2007/0215206 | A1 * | 9/2007 | Lull .................... G01F 25/0007 137/10 |
| 2008/0156896 | A1 * | 7/2008 | Anderson ............ B65D 83/262 239/34 |
| 2010/0272599 | A1 | 10/2010 | Broncano Atencia et al. |
| 2011/0266359 | A1 | 11/2011 | Haran |

OTHER PUBLICATIONS

Heilig, M., "Chapter 22, Beginnings: SEnsorama and the Telesphere Mask," in Digital Illusion, (Ed.: C. Dodsworth Jr.) ACM Press, New York, 1998, pp. 343-351.
Jin, et al., "Fe—Cr—Co Magnets (Invited)", IEEE Transaction on Magnetics, MAG-23, Sep. 1987, pp. 3187-3192.
Jin, et al., "Low Cobalt Cr—Co—Fe Magnet Alloys by Slow Cooling Under Magnetic Field", IEEE Transaction on Magnetics, MAG-16, May 1980, pp. 526-528.
Jin, et al., "Magnetic Sensors Using Fe—Cr—Ni Alloys with Square Hysteresis Loops", J. Appl. Phys. 55, Mar. 15, 1984, pp. 2620-2622.
McCloy, et al., "Science, medicine, and the future, Virtual Reality in Surgery", BMJ, Oct. 20, 2001, 323, pp. 912-915.
Nehaoua, et al., "Design and Control of a Small-Clearance Driving Simulator," IEEE Transactions on Vehicular Technology, Mar. 2008, 57, pp. 736-746.
Sastry, et al., "Virtural Environments for Engineering Applications," Virtual Reality, 1998, 3, pp. 235-244.
Tortell, et al., "The Effects of Scent and Game Play Experience on Memory of a Virtual Environment," Virtual Reality 2007, 11, pp. 61-68.
Yamada, et al., "Wearable Olfactory Display: Using Odor in Outdoor Environment," Proceedings of the IEEE Virtual Reality Conference, 2006, 8 pages.
Zyda, "From Visual Simulation to Virtual Reality to Games," IEEE Computer, Sep. 2005, 38, pp. 25-32.
Extended European Search Report for European Patent Application No. 14787744.3; dated Jan. 9, 2017; 7 pages.
Chinese First Office Action for Chinese Patent Application No. 201480035714.4; dated Feb. 15, 2017; 7 pages.
International Search Report and Written Opinion of International Application No. PCT/US2014/035054; dated Sep. 3, 2014; 11 pages.
Chinese Second Office Action for Chinese Patent Application No. 201480035714.4, dated Oct. 18, 2017, 17 pages.

\* cited by examiner

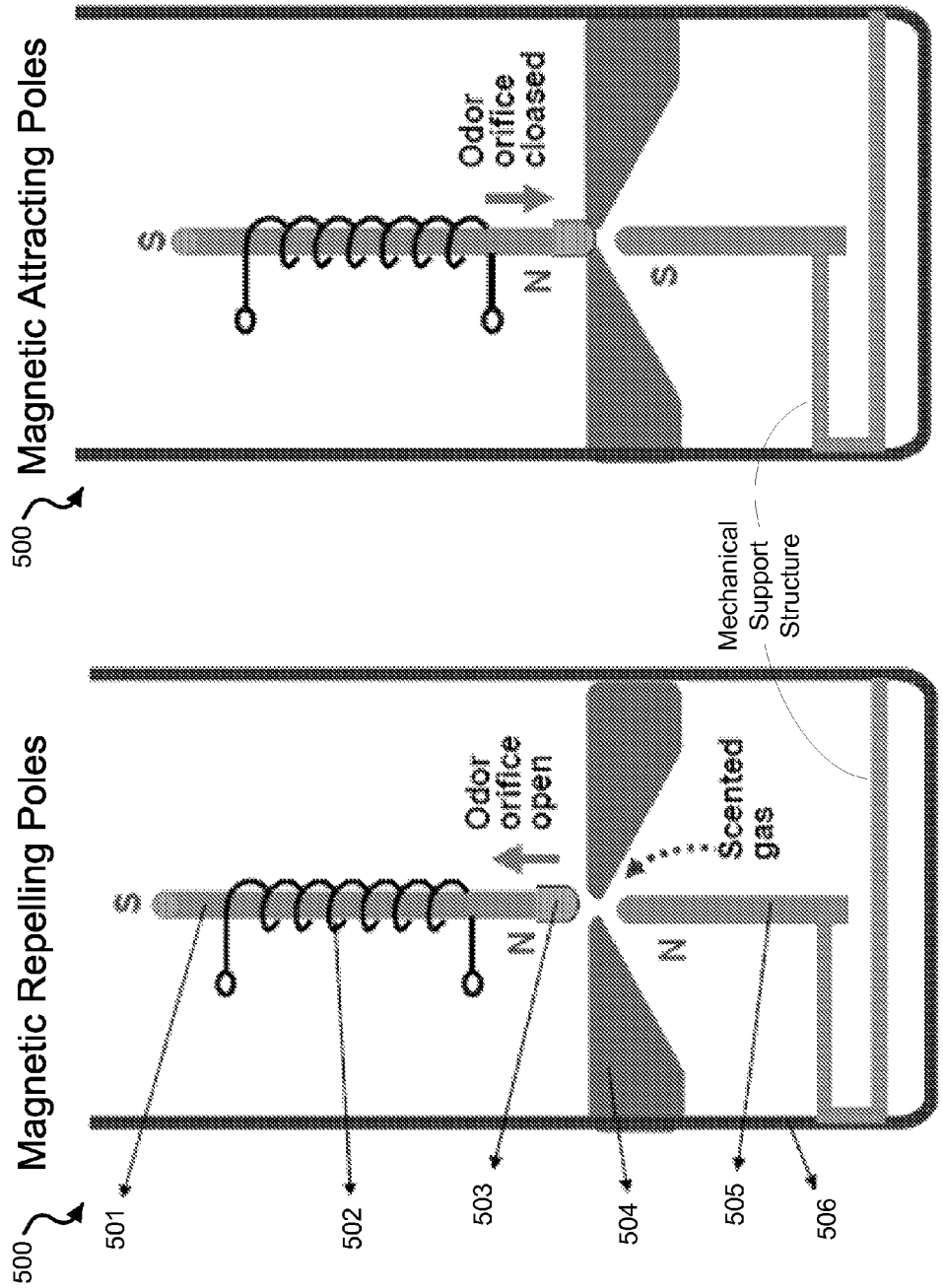

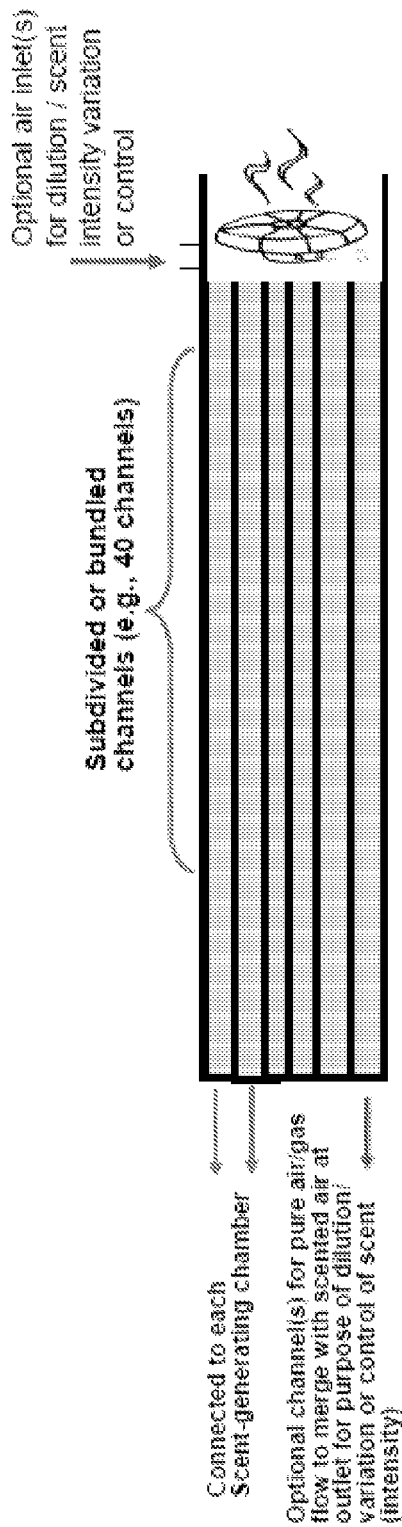
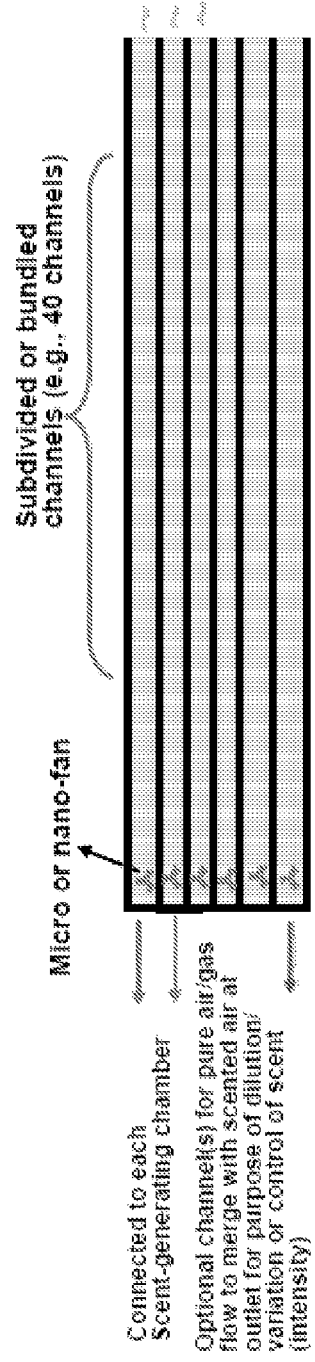
FIG. 8A
FIG. 8B

SWITCHABLE GAS AND LIQUID RELEASE AND DELIVERY DEVICES, SYSTEMS, AND METHODS

CROSS-REFERENCE TO RELATED APPLICATIONS

This patent document is a 35 USC § 371 National Stage application of International Application No. PCT/US2014/035054 filed Apr. 22, 2014, which further claims benefit of priority of U.S. Provisional Patent Application No. 61/814,810, entitled "SWITCHABLE GAS AND LIQUID RELEASE AND DELIVERY DEVICES, SYSTEMS, AND METHODS" and filed on Apr. 22, 2013. The entire content of the aforementioned patent applications are incorporated by reference as part of the disclosure of this patent document.

TECHNICAL FIELD

This patent document relates to systems, devices, and methods for release and delivery of gas, vapor, and liquid substances.

BACKGROUND

Augmented reality is a direct or indirect experience by an individual to supplement elements into the user's perception of a physical, real-world environment. Typically, augmented elements include sensory input, e.g., such as sound, video or graphics, scents or smells, or other. In contrast, virtual reality is an experience by an individual where the real environment is replaced by a simulated one.

Various technologies have been developed for producing virtual and augmented reality and multi-sensory applications for entertainment, education, engineering, advertising, biomedical and medicine including remote surgery, military, and other purposes. For example, technologies that can provide sensory effects to the user or observer, e.g., including haptics, scents, wind or mist, have been introduced into virtual reality and entertainment applications for the purpose of creating the feeling of greater realism and for providing for a more immersive experience. Design of scent delivery devices that allow reliable, rapid switching of scented air flux in a repeatable manner by synchronizable, remote actuation could have a significant impact on the effectiveness of the virtual, sensory, immersive, or augmented reality experience. Furthermore, such devices should offer practical, economic, scalable, mechanically and electrically reliable, and efficient on-demand control and precision-timed scent delivery for effective use by individual users or groups.

SUMMARY

Techniques, systems, and devices are disclosed for rapidly and easily switching the dispensing and delivery of fluids (e.g., liquids, vapors, or gas) on-demand.

The present technology includes techniques, systems, and devices to provide highly scalable, multiple-gated, odor/scent release and delivery, including rapid switching for on-demand dispensing of such scented substances. In some implementations, for example, the disclosed techniques, systems, and devices deliver a scented gas into a localized space (e.g., such as the headspace of an individual), which can enhance virtual or augmented reality entertainment.

The subject matter described in this patent document can be implemented in specific ways that provide one or more of the following features. For example, the disclosed technology includes devices that allow convenient, remote, electrically actuatable odor-release switches, such as based on latchable magnetic switches, piezoelectric, or thermally actuatable devices. For a capability to selectively release one or more of many different types of gases or liquids, X-Y matrix operational release systems are also disclosed. The disclosed technology is capable of miniaturizing scent delivery apparatuses, systems, and/or mechanisms while maximizing the number of different scents that can be stored, dispensed and cycled or sequenced in automated fashion or on demand. Exemplary applications of the present technology include the delivery of a scented gas into a localized space (e.g., such as the headspace of an individual) that is highly suited, among other things, to sensory or virtual or augmented reality experiences and entertainment.

In one aspect, a scent deliver device is provided to include a cartridge structured to store one or more scented substances; a transporting channel coupled to the cartridge to receive and transport the one or more stored scented substances and configured to include an end opening for releasing the transported one or more stored scented substances; and an actuator switch coupled to the transporting channel and operable to move between an open position and a closed position based on an applied signal to selectively allow passage of the one or more scented substances to the opening.

Those and other features are described in greater detail in the drawings, the description and the claims.

BRIEF DESCRIPTION OF THE DRAWINGS

FIGS. 5A and 5B show schematic illustrations of an exemplary vertically positioned magnetically latchable switch in a scent transport compartment.

FIGS. 8A and 8B show schematic illustrations of an exemplary single-fan and multi-fan enhanced operation of scent transport via a nano- or micro-scale channels in an exemplary multi-channel transporting channel array.

DETAILED DESCRIPTION

Figure 1:
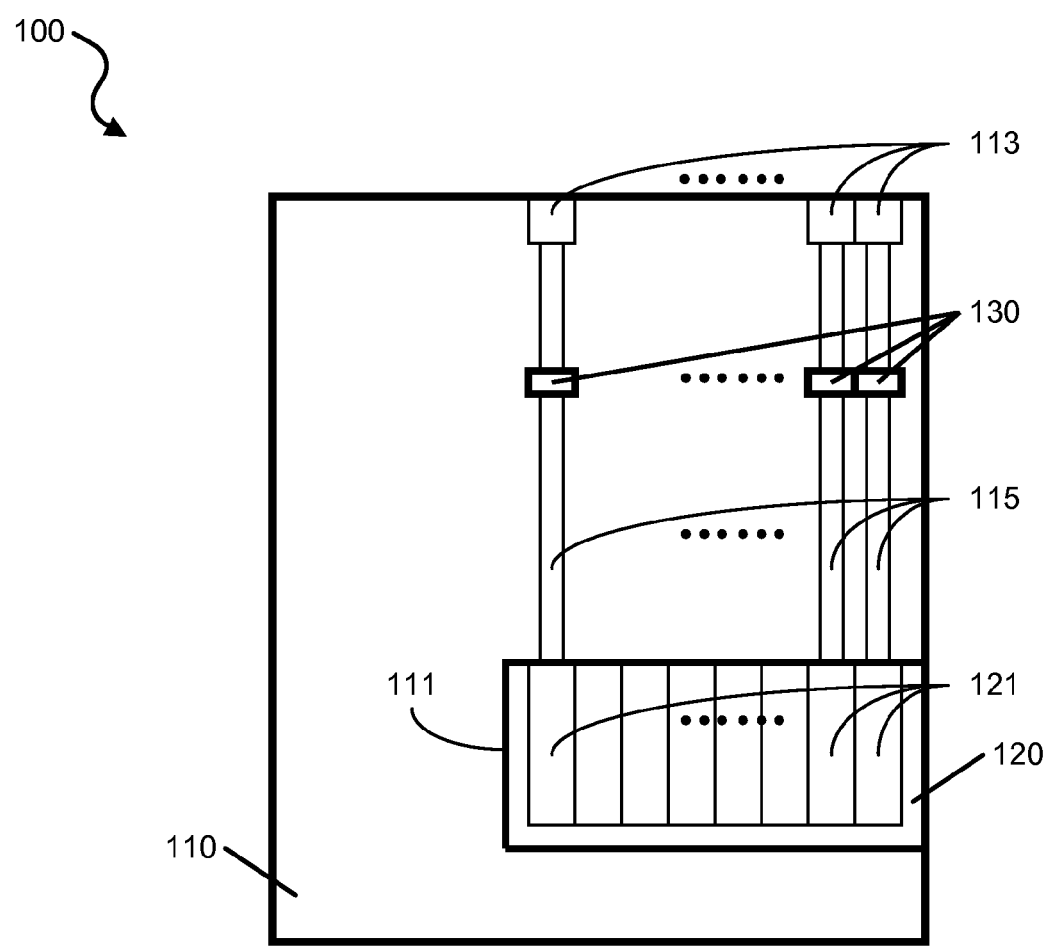
FIG. 1 shows a block diagram of an exemplary scent delivery device of the disclosed technology.

Disclosed are highly scalable techniques, systems, and devices for on-demand dispensing and delivery of scented substances, e.g., including liquids, vapors or gas. Scent delivery devices of the disclosed technology include convenient, remote, electrically actuatable scent-release components based on, e.g., latchable magnetic, piezoelectric, or thermally actuatable switches and mechanisms. In some implementations, for example, the scent delivery devices include nanoscale and microscale material structures to control formation and/or delivery of fluids (e.g., such as liquids, vapors, or gases) to produce the scented substances. In some implementations, for example, the disclosed technology provides capability to selectively release one or more of many different types of gases or liquids, e.g., using X-Y matrix operational release systems. The present technology offers the miniaturization of the scent delivery mechanism while maximizing the number of different scents that can be stored, dispensed, and cycled or sequenced in an automated fashion and/or on demand. Applications of the present technology include, but are not limited to, the delivery of a scented gas into a localized space (e.g., such as the headspace of an individual) that is highly suited, among other things, to virtual, sensory, or augmented reality experiences and entertainment.

By increasing the potential number of different scents for relatively rapid sequential delivery, e.g., the disclosed scent delivery devices offer the possibility of more complex and sophisticated sensory (olfactory) communication, sampling, branding or advertising, as well as greater dramatic possibilities and/or enhanced realism within a virtual or augmented reality or sensory experience. For example, in some cases, the disclosed devices can be used as an olfactory display or as a caller identifier in a mobile phone. In other examples, the disclosed devices can be used in motion pictures or videogames (e.g., by way of a wide range of multi-scent tracks available for delivery timed coincident with scenes, actions or elements of drama). Other exemplary applications of nano- or micro-device control and on demand delivery of scented gas or liquids include, for example, (a) point of sale or augmented reality advertising; (b) scented packaging; (c) fragrance-emitting jewelry embedded with the mechanism/device to dispense and cycle different perfumes, selected, set by or reacting to biofeedback of the wearer, in which the mechanism generates an invisible cloud of scent in or around the immediate space near or around the wearer; (d) air fresheners in small, enclosed spaces such as shelving or other furnishings, or that can be attached to fixtures; (e) olfactory branding or signaling; (f) military applications for control or influence of individual behavior; (g) aromatherapy; (h) medical therapy, drug delivery or remote or virtual surgery; (i) hygiene; (j) education; and/or (k) use in multi-sensory apparatuses providing neurological, multi-modal effects, among other applications.

The disclosed technology provides several advantages. One exemplary advantage of the present technology is the versatile design using a simplified valve-containing dispensing or valveless dispensing that allows the choice of scents (e.g., including chemicals in a carrier gas) by the user on demand. Such designs include exemplary 'latachable-switch gating' mechanisms of the disclosed technology. For example, these exemplary gating mechanisms not only replaces the need for complicated mechanical valves, but also minimizes the electrical input necessary to control the gating, and is also scalable to small dimensions, e.g., including on a millimeter scale, thereby adding to the reduction in size and weight (and portability, placement or wearability) of a device or apparatus embodying the technology.

Some existing systems utilize a valveless system capable of dispensing small volumes of scents into a localized space, however, the technical requirements of the dimensions of the delivery capillaries diameters and lengths are, in themselves, limiting. An advantage of the present technology is that there are no such limitations. Some other existing systems that use a valveless technology employ a primary method of evaporating and dispensing a scented gas via a heating element whose time required to create a required volume of scented gas is comparatively disadvantaged to the present technology whose mechanisms enable the rapid generation of a scented gas. These and other existing scent generating devices also have limitations in terms speed, dimension, selectivity and durability. Also, existing technologies currently employed to selectively release scents into a localized space, or headspace, are limited by the number of different scents capable of being cycled or sequenced, timed and controlled for on-demand precision delivery. Moreover, machines that do have scalable multi-scenting capability and precision timed control and delivery of scented gas into a headspace (or to the nose) such as olfactomers are relatively large in size and are not portable or wearable.

The disclosed technology can also include the use of 'cold diffusion' technology, which, for example, generates a scented gas without the use of heating as a primary mechanism to evaporate a scent-carrying liquid. Delivery of evaporated scent via the present technology also obviates the inherent deposition and other disadvantages and risks in delivering atomized scent at close range to an object or individual. Cold diffusion also avoids certain limitations or drawbacks associated with using heating as the primary mechanism to evaporate a liquid, including the energy required to achieve fast evaporation for rapid gas formation and delivery, and undesirably altering the properties or behavior of the scent-generating chemical components by heating.

Other primary mechanisms for generating an evaporated (e.g., completely evaporated) scented gas can include the passage of air on the surface of a scented solvent or other material, or through a porous solid, gel or other scented substance. In the present technology, for example in one embodiment, microbubbles of air are created and pumped through a solvent or oil containing scented material and generating a scented gas upon exit at the surface of the solvent or oil. The use of microbubbles in such a way maximizes the potential for large surface area contact of air (or gas) within the scented solvent or oil, thereby increasing potential diffusion, and as a result reducing the time necessary to deliver a desired volume of scented air.

Most examples of existing selective scent releasing and delivery systems introduced to-date are limited by either ineffective control, lack of precision timing deliverable to the intended target, unwanted mix of scents during sequenced delivery, lingering scent in the environment, the mechanical reliability, energy efficiency and/or the cost and size of the delivery apparatus. Diffusion of a large volume of scent into a large area is comparatively difficult to quickly clear from the air (or dissipate), thereby limiting the rapidity with which a succeeding scent can be delivered 'cleanly' to individuals within the space. For entertainment applications, for example, in many instances scented air is released into the general space of a theater via the ventilation system or fans, or in and around seating. Such conventional delivery mechanisms inherently have limited or no multiplexing capabilities, nor can they provide rapid scent delivery capability precision-timed to the headspaces of individuals. Further, the existing systems have difficulty providing simultaneous scented air delivery (of uniform distribution) to each member of an audience, in synchrony with a specific event or time within an audiovisual presentation such as a motion picture or videogame. Examples of existing systems that can release scent within seating area include the Sensorama game system from which a scent is released from the chair according to the displayed scene and the steering wheel can provide mechanical vibrations. In movies such as those in the AMLUX theatre, scents were released in conjunction with visual images. Scent release by evaporating or spraying a scented material has been utilized for the training of fire-fighters and scent-emitting collars have been employed for the training of soldiers. However, many of these known approaches are impractical, operationally unreliable, or limited in their capacity for precision-timed, multiplexing scent delivery. Therefore, there is a need for a reliable scent release and delivery system having rapidly switchable, automated and/or remote, actuatable and multi-cycle durable characteristics, that incorporate x-y matrix operational systems enabling controlled, timed scent release from many different sources of scents (with a minimal number of controlling mechanisms).

Referring to the drawings, FIG. 1 shows a block diagram of an exemplary scent delivery device 100 of the disclosed technology. The device 100 includes a housing or casing unit 110 structured to include a compartment 111 to hold a cartridge 120 containing one or a plurality of scented substances. The scented substances can include any of a variety of fluids, e.g., including a liquid, a gas, or a vapor. The housing 110 of the device 100 is structured to include one or more openings 113 to allow the scented substances to dispense to an outer environment from the device 100. The housing 110 of the device 100 is structured to include one or more transporting channels 115 formed between the compartment 111 and the opening(s) 113. In various exemplary embodiments of the device 100, a transporting channel 115 is configured to deliver or accelerate a scented substance from a storage chamber, e.g., of the cartridge 120, to the opening 113. The cartridge 120 supplying the scented substances to the scent delivery device 100 can be structured to include one or more chambers 121 containing the one or more scented substances, for example, where a particular scented substance can be contained in a particular corresponding chamber. The device 100 can be implemented to control the delivery of one or more of the scented substances to the outer environment, e.g., including a headspace of a user. To provide such control, the device 100 includes one or more actuator switches 130, in which an actuator switch 130 is arranged in a corresponding transporting channel 115 and operable to move between an open position and a closed position based on an applied signal to selectively allow passage of the scented substance to flow through and/or from the corresponding transporting path 115. The actuator switches 130 of the device 100 can include a magnetic actuated gating switch mechanism, a piezoelectric actuated gating switch mechanism, and/or a thermal actuated gating switch mechanism or device of the disclosed technology. Examples of the magnetic, piezoelectric, and thermal actuated switch mechanisms and devices are described herein.

Figure 2A:
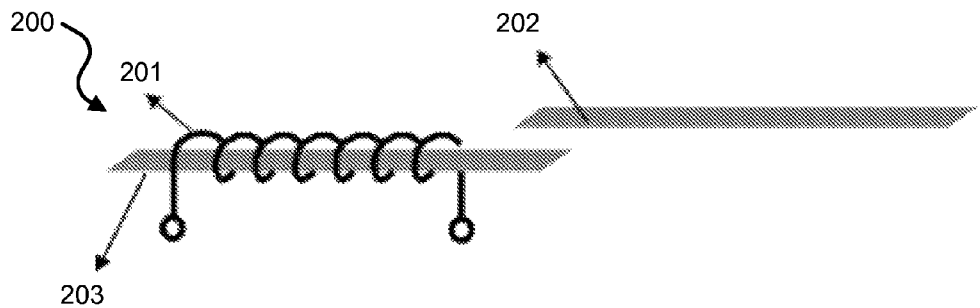
FIG. 2A shows a schematic diagram of an exemplary magnetically actuated latchable switch of the exemplary scent delivery device.

FIG. 2A shows a schematic illustration of an exemplary magnetically actuated latchable switch 200 of the disclosed technology. For example, the magnetically actuated latchable switch 200 can be positioned in the device 100, e.g., in the transporting channel 115, so that the flow of the scented substance can be regulated by actuation of the switch 200. The magnetically latchable switch 200 includes a latchable (square M-H loop) magnetic alloy cantilever 203, which is surrounded by a solenoid 201 to supply a pulse current to instantaneously magnetize the cantilever 203. For example, the latchable square M-H loop cantilever 203 can be configured to be 0.05-0.5 mm thick, 0.1-2 mm wide, 1.0-5 mm long). For example, the mini solenoid 201 can be configured around the cantilever 203 including 1000 turns. The magnetically latchable switch 200 includes a mating cantilever 202 that contacts the cantilever 203 in a closed position (e.g., at a first magnetic state) and moves away from the cantilever 203 in an open position to provide an opening or orifice (e.g., at a second magnetic state).

The exemplary magnetically latchable switch 200 can open or close with a single pulse magnetic field, e.g., supplied with a pulse current. The latchable (square M-H loop) magnetic alloy cantilever 203 is placed inside a mini solenoid to supply the pulse current to instantaneously magnetize the cantilever. For operation of the magnetic latchable switch 200, the mating magnetic cantilever 202 is arranged to couple to the cantilever 203 in the closed position, and can be configured as a stationary magnet or as a movable cantilever. The mating magnetic material 202 can be a soft magnet (e.g., a permalloy, for example, having 80% Ni-20% Fe in weight % or 45% Ni-55% Fe, or a silicon steel, or other), a semi-hard magnet (e.g., Fe—Cr, Fe—Ni, and other magnetic alloys), or a permanent magnet (e.g., Fe—Cr—Co, Vicalloy, Sm—Co coated cantilever).

The magnetic properties of a magnetic material can be described by several parameters, e.g., including a saturation magnetization (Bs) that indicates the highest possible magnetization value in the given material, the remanent magnetization (Br) that indicates the remaining magnetization value after the applied field is removed to zero field, and the coercive force (Hc) which is an indication of a required external applied magnetic field that needs to be applied to reduce/force the magnetization of the material to zero, which indicates how hard or soft the magnetic material is.

Figure 2B:
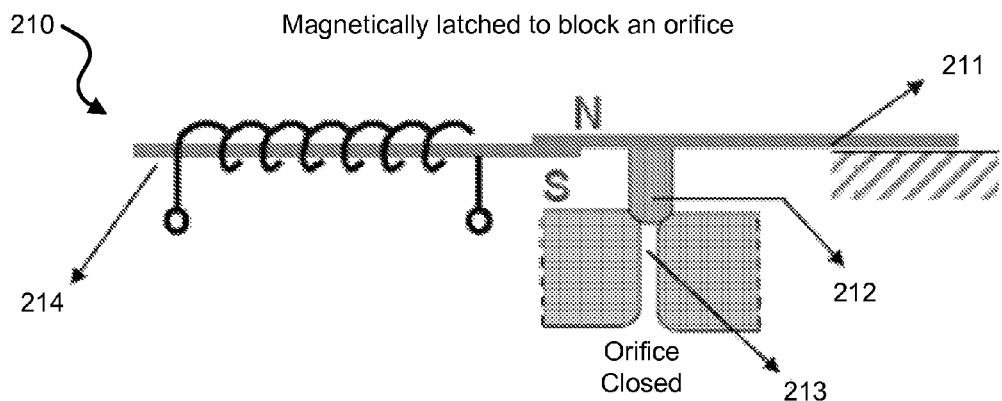
FIGS. 2B and 2C show schematic diagrams of another exemplary magnetically latchable switch for closing and opening of an orifice to control dispensing of a scent.
Figure 2C:
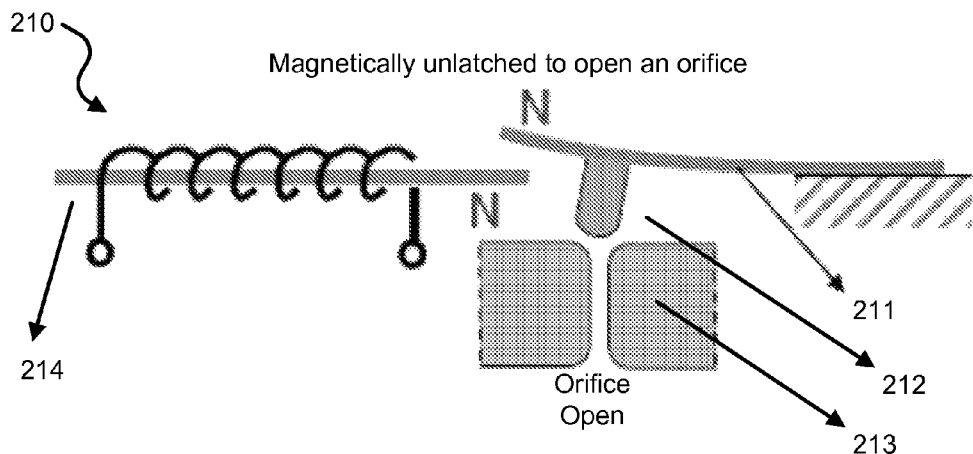

FIGS. 2B and 2C show schematic diagrams of another exemplary magnetically latchable switch 210 for closing and opening of an orifice to control dispensing of a scent. The magnetically actuated latchable switch 210 can be composed of two mating magnetic components that can be independently controlled by externally applied pulse magnetic field, for example, by sending an electric current through a solenoid to cause one of the magnetic component to move from one position to another, e.g., to and from an open and a closed position. For example, the magnetically actuated latchable switch 200 can be positioned in the device 100, e.g., in the transporting channel 115, so that the flow of the scented substance can be regulated by actuation of the switch 200.

As shown in FIG. 2B, the two magnetic mating components 211 and 214 of the magnetically latchable switch 210. The magnetic component 214 can be configured as a solenoid like that of the latchable (square M-H loop) magnetic alloy cantilever 203 and solenoid 201 of FIG. 2A, in which the magnetic component arm 214 can be magnetized based on an applied electrical pulse current. The switch 210 includes a tip or plug 212 attached to the magnetic component arm 211, which contacts a ring or component 213 having an orifice to allow passage of the scented substance. The tip 212 contacts the plug 213 in the closed position such that the tip 212 blocks the orifice and prevents the scented substance from flowing through. The tip 212 is moved out of contact with the plug 212 when the magnetic component arm 211 is moved.

Figure 3A:
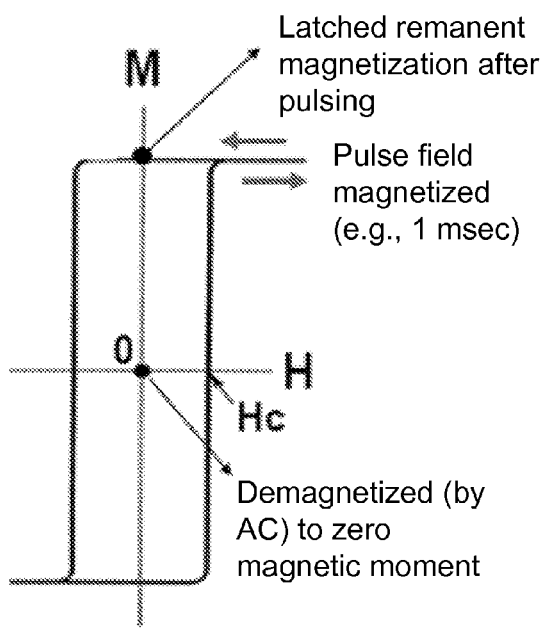
FIG. 3A shows a magnetization plot of an exemplary square loop magnetic material with optimally low magnetic coercivity suitable for the exemplary magnetically actuated latchable switch.
Figure 4:
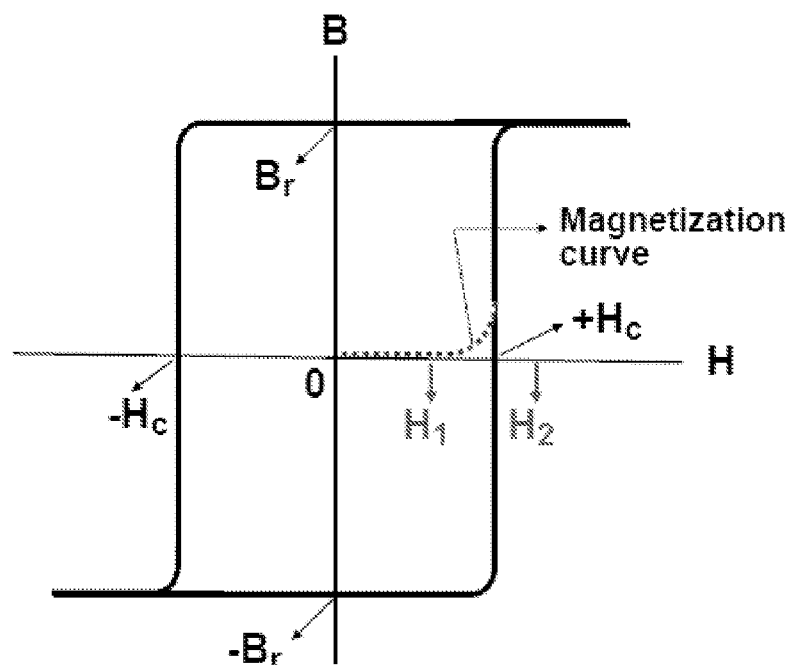
FIG. 4 shows a magnetization plot showing magnetic switching in an exemplary square loop magnetic loop material.

For example, when the square loop, magnetically latchable wire or ribbon of the magnetic component 214 is pulse magnetized to the high-magnetization remanent state of Br, as shown in FIG. 3A and FIG. 4, the magnetized member in the solenoid attracts the soft magnet (or hard magnet) cantilever 211 so that the exemplary mechanically soft, elastomer-tip 212 of the cantilever 211 is moved down to contact the plug 213 and block the orifice from allowing the scent to flow through, as illustrated in FIG. 2B. For example, the tip 212 can be formed of a mechanically soft material including a suitable elastomeric material, e.g., such as polydimethylsiloxane (PDMS). When the magnetically latchable wire or ribbon in the solenoid is demagnetized, e.g., by a short 60 Hz gradually diminishing field applied by the solenoid (e.g., using gradually reduced current, for example, 0.1-1 second), the magnetization of the wire or ribbon in the solenoid is reduced to near zero, which is represented at the origin of the plot in FIG. 3A or FIG. 4. The magnetic attractive force between the two mating cantilevers 211 and 214 is reduced well below the critical force required to overcome the mechanical spring force that tends to keep the cantilevers straight. The magnetic cantilever 211 is then released and the orifice is opened. In some implementations, for example, the magnetic cantilever 211, if it is made of a soft magnet alloy, can be pre-curvatured or positioned spaced apart (e.g., such that the two cantilevers can be parallel pre-positioned with a spacing gap of 0.1-2 mm), and the two cantilevers can be separated (switch open) by the elastic restoring spring force. Alternatively, if the magnetic cantilever 211 is made of permanent magnet, the cantilever 214 in the solenoid is magnetized to an opposite magnetic polarity by applied pulse magnetic field (e.g., by DC pulse electric current applied to the surrounding solenoid) to actively repel each other. There are several exemplary variations of switch open vs. close operations that can be utilized depending on the specific operational needs and the nature of the magnetic cantilever materials utilized.

The exemplary magnetically latchable, scent release switch that can open or close with a single DC pulse magnetic field is highly practical and energy-saving, as a continuous supply of electric current to keep the valve open or closed would consume much energy and can also cause undesirable heating of the scent delivery device 100. For example, an exemplary DC pulse of the applied current can be configured to be shorter than 1 second, e.g., in some implementations shorter than 0.1 second, and in other implementations, for example, less than 0.01 second. For example, the magnitude of the applied magnetic field can be configured to be at least 30% higher than the coercive force of the core magnetic material within the solenoid, e.g. in some implementations at least 50% higher, and in other implementations, for example, at least 100% higher than the coercive force of the magnetic material within the solenoid.

In some implementations of the exemplary latchable-switch gating mechanism, a brief pulse type magnetic field (e.g., generated by applied current to the solenoid) can be utilized to produce the latchable magnetic response of the magnetically actuated latchable switch, e.g., such as the exemplary switch 200 and 210. Notably, such operation can be implemented instead of a continuous application of the energy-consuming electric current and hence a continuous application of the magnetic field. For example, the pulse magnetic field needs only to be applied just once for magnetization. However, for the sake of ensuring the proper magnetization, the DC current pulse may optionally be applied more than once. An application of multiple pulses less than 10 times can be acceptable, in which the multiple pulses can be applied to ensure the magnetic switching.

Figure 3B:
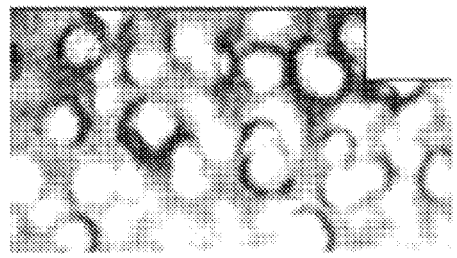
FIGS. 3B and 3C show images of exemplary square loop magnetic material structures by spinodal decomposition of Fe—Cr—Co alloy to produce spherical Fe-rich, strongly magnetic phase followed by uniaxial plastic deformation to elongate the phase to impart shape anisotropy.
Figure 3C:

FIG. 3A shows a magnetization plot of an exemplary square loop magnetic material with optimally low magnetic coercivity suitable for the exemplary magnetically actuated latchable switch. FIGS. 3B and 3C show images of exemplary square loop magnetic material structures by spinodal decomposition of Fe—Cr—Co alloy to produce spherical Fe-rich, strongly magnetic phase followed by uniaxial plastic deformation to elongate the phase to impart shape anisotropy.

As shown in FIG. 3A, an important feature for the exemplary solenoid configuration of the magnetic latchable switch is the square loop of the magnetic element in the solenoid. The latchable nature of the scent release/close switch is important for practical applications. As such, in such exemplary implementations, a switch open/close operation can be performed with a single short DC pulse of, e.g., 0.01-5 milliseconds: the electrical energy used is relatively small since the electrical current does not need to be supplied once the switch open/close operation is done in a millisecond level time frame. The demagnetization to remove much of the previous magnetization, for example, to male two magnetically attached components to be separated, can be accomplished by gradually diminishing the AC magnetic field applied by the solenoid current, which can also be very fast, requiring between a 0.1-1 second time frame, for example, for 60 Hz AC current signals. For example, to minimize solenoid heating and magnetic material heating on AC current and AC magnetic field application, the number of demagnetizing cycle can be performed in less than 1 second, and in some implementations, for example, preferably less than 0.3 seconds.

According to the disclosed technology, for example, the desired squareness of the B—H loop (the Br/Bs ratio of the remanent magnetization Br in the absence of applied field vs. the magnetic saturation magnetization Bs) in the latchable magnetic cantilever material can be configured to be at least 0.8 for efficient operation of latchable scent release or scent blockage functionality of the magnetically latchable switch. In some implementations, for example, the squareness of the B—H loop can be configured to be at least 0.9, or in some implementations, for example, at least 0.95.

For example, to guard against inadvertent magnetic switching by stray field and unintended scent release, the coercive force Hc can be configured to be at least 10 Oe, and in some implementations, for example, at least 20 Oe, and even in some implementations, for example, at least 40 Oe. In order to perform the magnetization and magnetic switching with a reasonable, overly excessive magnetic field, the desired Hc should also be preferably less than 100 Oe, and in some exemplary cases, less than 50 Oe.

For example, in order to obtain such a latchable magnetic material, a magnetic alloy, preferably ductile and plastically formable alloy, can be subjected to materials processing of anisotropic uniaxial deformation, e.g., such as wire drawing, swaging, extrusion, and cold working. An example is an Fe-25-35% Cr-6-12% Co alloy that can be spinodally decomposed to have a two phase structure including near-spherical Fe, Co-rich, stronger magnetic phase nanoparticles, as shown in FIG. 3B, embedded in a weakly magnetic or nonmagnetic matrix phase, so that subsequent processing can produce desirable switchable magnetic behavior of the material. The spherical magnetic phase can then be elongated by uniaxial plastic deformation of the alloy wire or rod, as shown in FIG. 3C, which provides a shape anisotropy and square loop with the Br/Bs squareness ratio in excess of 0.8-0.9. The coercive force Hc can also be enhanced to any value from 30-500 Oe depending on the duration of heat treatment. As the preferred Hc is an intermediate value, it is desirable to shorten the heat treatment process in such a way to provide Hc of less than 100 Oe, and in some implementations, for example, less than 50 Oe. The exemplary spinodal alloys such as Fe—Cr—Co also respond to the magnetic field heat treatment in the presence of magnetic field of, e.g., 300-100 Oe, and provides square loop magnetic properties.

Other latchable magnet alloys can also be designed and fabricated, for example, alloys such as Fe-20% Cr, Fe-20% Cr-4% Ni, Fe-15% Cr-3% Mo can be uniaxially deformed to produce latchable semi-hard magnet alloys. Examples of such alloys are described in the following articles: "Fe—Cr—Co Magnets", IEEE Trans. Magn. MAG-23, 3187-3192 (1987); "Low Cobalt Cr—Co—Fe Magnet Alloys by Slow Cooling Under Magnetic Field", IEEE Trans. Magnetics, MAG-16, 526-528 (1980); and "Magnetic Sensors Using Fe—Cr—Ni Alloys with Square Hysteresis Loops", J. Appl. Phys. 55, 2620-2622 (1984). These articles are incorporated by reference as part of the disclosure of this patent document.

FIG. 4 shows a magnetization plot showing magnetic switching in an exemplary square loop magnetic loop material. As depicted in FIG. 4, the magnetization change from the demagnetized state (the origin) follows the dotted curve as the applied magnetic field is increased. From the oppositely magnetized state (the −Br state), the magnetization change upon applying a positive magnetic field follows the solid curve. Therefore, the applied field $H_1$ cannot switch the magnetization direction from the zero magnetization (the origin) or from −Br state to +Br state while the applied field $H_2$, being larger than the coercive force Hc, can switch the magnetization. Only when the applied magnetic field is greater than the coercive force, a new latchable magnetization (+Br or −Br) is attained.

The latchable scent release switch can be positioned horizontally with respect to the transporting channel, e.g., as shown in the exemplary configurations of FIGS. 2A-2C, as well as be positioned vertically with respect to the transport channel. For scent controlled-release and delivery devices employing multi-channels, the vertical arrangement may be preferred. FIGS. 5A and 5B show schematic illustrations of an exemplary vertically positioned magnetically actuated latchable switch 500 in a scent transporting channel or compartment. FIG. 5A shows an exemplary configuration of the magnetically latchable switch 500 in which magnetically repelling poles of the switch are actuated to open the switch, and FIG. 5B shows an exemplary configuration of the magnetically latchable switch 500 in which magnetically attracting poles are actuated to open the switch. For example, an applied field greater than the coercive force Hc can switch the magnetization to actuate the switch.

As shown in FIGS. 5A and 5B, the magnetic actuator switch includes a transfer channel path 506 for a scented substance to flow through. The magnetic actuator switch includes a magnetically latchable and vertically-movable component 501, e.g., such as a pole, rod, or other shaped structure, aligned vertically within the channel 506. In some examples, the vertically-moveable component can be configured with lubricated guide. The magnetic actuator switch includes a solenoid wrapped around the component 501 to pulse magnetize the component 501. The magnetic actuator switch includes a complaint tip 503 on one end of the component 501. In some implementations, for example, the compliant tip 503 can be formed of PDMS. The magnetic actuator switch includes a soft orifice-having structure 504 configured in the transport channel and structured to include an orifice that allows the scented substance to flow through the channel. For example, the soft orifice-having structure 504 can be formed of PDMS. The component 501 is positioned on one side of the structure 504 such that the tip 503 is aligned with the orifice of the structure 504. The magnetic actuator switch includes a fixed magnetic component 505, positioned on the other side of the structure 504 and aligned with the orifice, such that the component 505 is on the opposing side to that of the component 501. For example, the solenoid (or ribbon) 502 of the magnetic component 501 can be connected to a conduit to supply an applied signal to magnetize the magnetic component 501. In some implementations, for example, the solenoid 502 can be connected to the wall of the channel path 506. For example, when the applied field is greater than the coercive force Hc, the magnetization polarity switching can activate and the latchable magnet position is obtained for closure or opening of the orifice.

For example, operation of the magnetically switchable and latchable gates require only a small amount of energy as the switch ON or OFF process takes a very short pulse current to complete the magnetic attraction or repulsion, e.g., such as 0.001 second to 1.0 second of electrical current application. Therefore, the use of energy by the exemplary device is minimal, and also such a short pulse operation allows the sending of a larger if needed, without excessively heating or burning the electrical circuits. The electric current or voltage can be supplied by other energy source, e.g., such as by using DC or AC electrical connections, batteries, supercapacitors, solar cells, or other energy-providing devices. The use of the mechanically compliant tip of the magnetically movable component in the exemplary embodiments of the magnetically latchable switch of FIGS. 5A and 5B or FIGS. 2B and 2C, for example, can include an elastomeric material to provide improved reliability of scent release and blocking operations. Yet in some embodiments, for example, the magnetically movable components may not include the mechanically compliant tip and can function to block and open the orifice.

In addition to the exemplary magnetically latchable switches as the open/closure mechanism, the disclosed technology also includes thermally actuated gating switch mechanism. One example is illustrated in FIGS. 6A-6B.

Figure 6A:
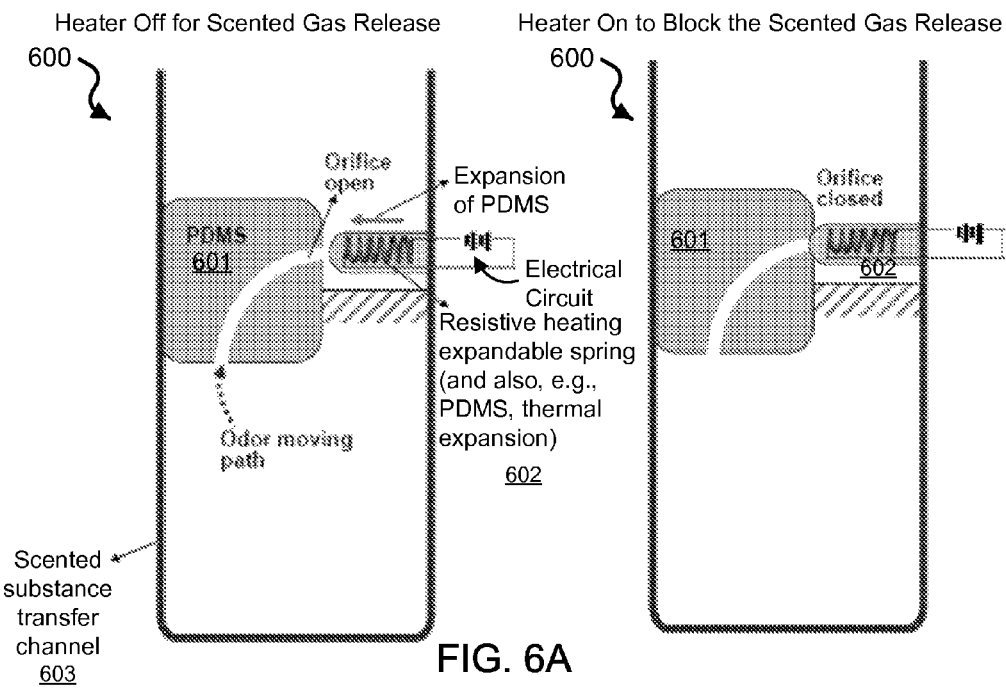
FIGS. 6A and 6B show schematic illustrations of an exemplary electrically activated local heater valve for scent release on/off switching operations.

FIG. 6A shows an illustrative diagram of an exemplary horizontally aligned thermal actuated gating switch mechanism 600 of the disclosed technology. The switch 600 includes a plug 601 (e.g., formed of PDMS) having an orifice that allows the scented substance to pass through, in which the plug 601 is arranged in a transporting channel, showed as scented substance transfer channel 603. The switch 600 includes a horizontally-moveable component 602 that moves to contact and not contact the orifice of the plug 601. The horizontally-moveable component 602 includes a spring that thermally expands when heated, e.g., by applying an electrical signal from a circuit to cause resistive heating of the spring component 602. For example, the applied electrical signal can be supplied by a variety of electrical energy sources including wall plug-in electricity, a battery, a supercapacitor, solar cells, or other energy-providing devices. In some implementations, for example, the component 602 includes a compliant tip that contacts the orifice of the plug 601, e.g., in which the tip can be formed of PDMS. The diagram on the left of FIG. 6A shows the applied signal 'off' so that no heat is generated by resistive heating expandable spring component 602, and therefore the switch 600 is open for release of the scented substance. For example, the spring 602 can include a PDMS coating, e.g. such as the tip, that can also be subjected to thermal expansion. The diagram on the right of FIG. 6A shows the applied signal 'on' so that heat is generated by resistive heating of the thermally expandable spring causing the component 602 to contact and block the orifice, and therefore the switch 600 is closed.

Figure 6B:
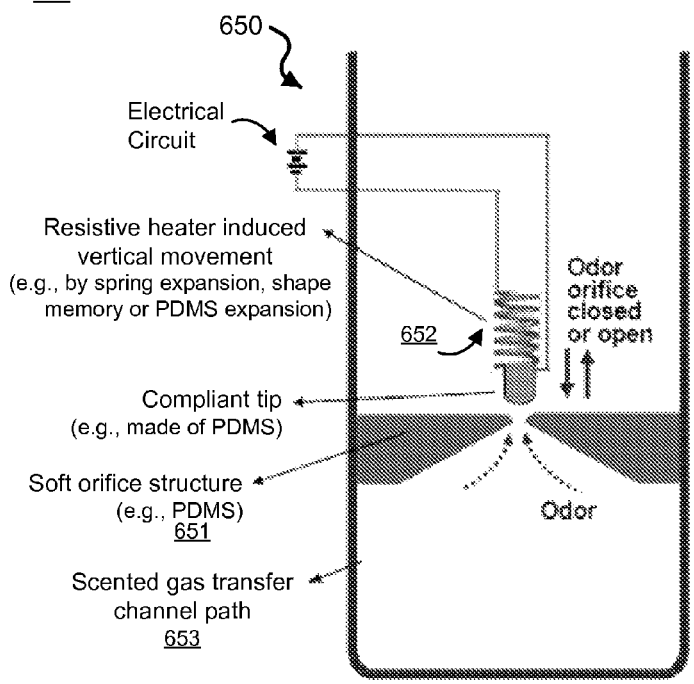

FIG. 6B shows an illustrative diagram of an exemplary vertically aligned thermal actuated gating switch mechanism 650 of the disclosed technology. The switch 650 includes a plug 651 (e.g., formed of PDMS) having an orifice that allows the scented substance to pass through, in which the plug 651 is arranged in a transporting channel, showed as scented substance transfer channel 653. The switch 650 includes a vertically-moveable component 652 that moves to contact and not contact the orifice of the plug 651. The vertically-moveable component 652 can include a spring that thermally expands when heated, e.g., by applying an electrical signal from a circuit to cause resistive heating of the spring component 652, and/or the component 652 can include a shape memory material. In some implementations, for example, the component 652 includes a compliant tip that contacts the orifice of the plug 651, e.g., in which the tip can be formed of PDMS.

For example, the thermal expansion material/structure can be combined with a tight-sealing tip material for efficient switching operation, e.g., such as e.g., such as PDMS or other suitable material. The resistive heating of an expandable spring in FIG. 6A causes the spring to move horizontally, e.g., in which the exemplary PDMS elastomer material surrounding the spring can also add to the thermal expansion, thus to help close the horizontal valve to close the odor orifice. For example, as shown in the exemplary vertical arrangement in FIG. 6B, for this thermal expansion valve to operate, the electrical current has to be maintained to keep the switch closed, which is in contrast to the disclosed magnetic latchable switch designs already described. The exemplary vertical arranged thermal actuator switch can be latchable in exemplary designs including a mechanical latch saw-tooth structure. For example, the degree of thermal expansion can be intentionally adjusted so as to make the moving portion click on a step-like mechanical latch, while additional thermal expansion, e.g., by a short period increased electrical heater operation to a higher temperature to move the spring part further to the left (e.g., this is allowable since the material is surrounded by mechanically soft and compliant PDMS elastomer) and release of the mechanical step saw-tooth latch so that the thermal contraction on ceased current flow brings back the moving part back to the right to open the valve.

Figures 7A, 7B:
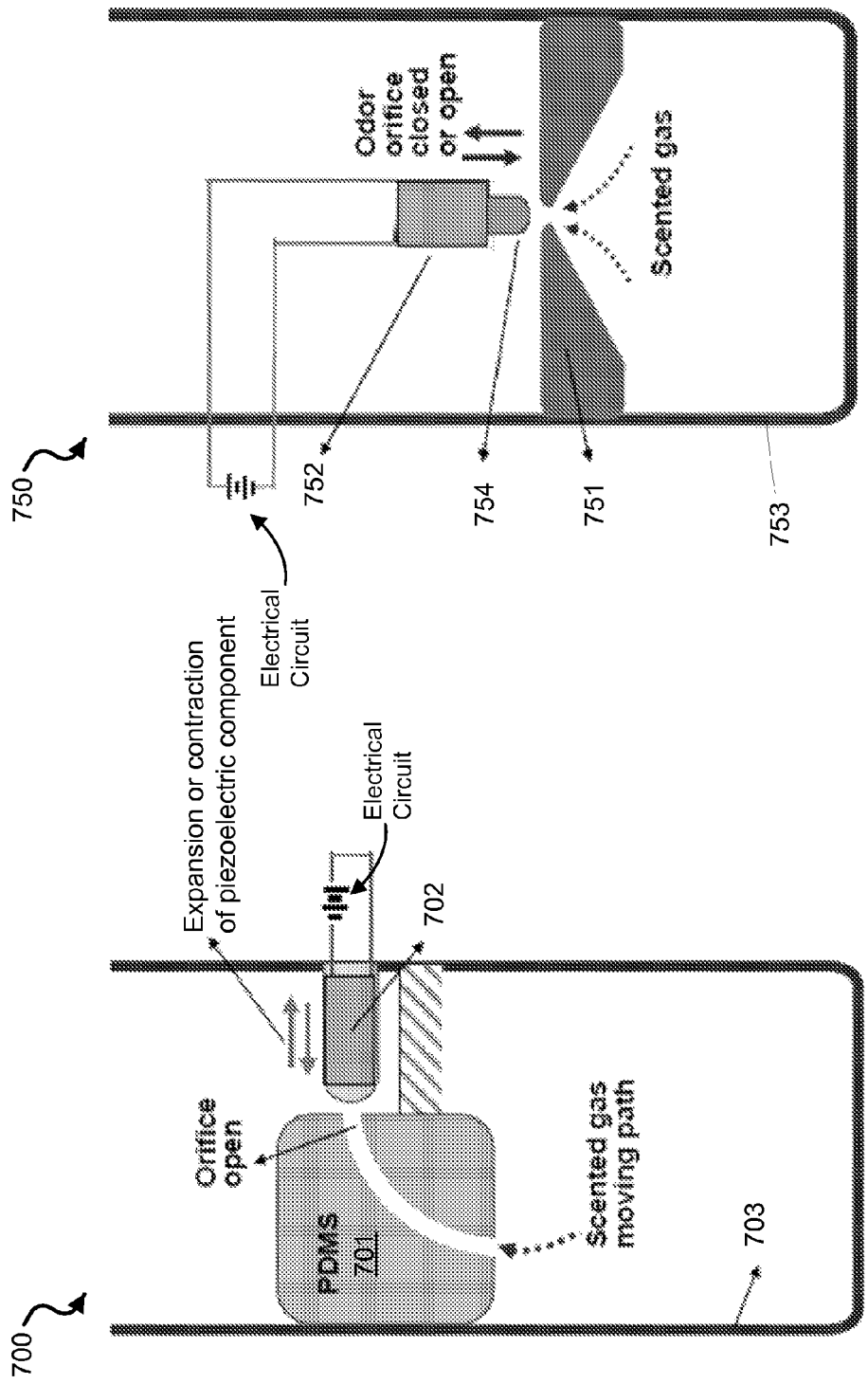
FIGS. 7A and 7B show schematic illustrations of an exemplary electrically activated piezoelectric valve for scent release on/off switching operations.

FIG. 7A shows an exemplary embodiment of a piezoelectric actuator switch 700 in a horizontal configuration in a transporting channel. The switch 700 includes a soft structure plug 701 (e.g., formed of PDMS) having an orifice to allow a scented substance to pass through, in which the soft structure plug 701 is arranged in a transporting channel, showed as the scented substance transfer channel 703. The switch 700 includes a horizontally-moveable piezoelectric component 702 that moves to contact and not contact the orifice of the plug 701. For example, the component 702 can move based on a piezoelectric effect of the material(s) of component 702 in response to an applied electrical voltage from an electrical circuit. The piezoelectric component 702 can be configured as an expandable and contractible component or as a cantilever bending to make the orifice or open.

FIG. 7B shows an exemplary embodiment of a piezoelectric actuator switch 750 in a vertical configuration in a transporting channel. The switch 750 includes a plug 751 which can include a soft structured material, such as PDMS) having an opening to allow a scented substance to pass through. The plug 751 is configured in a transporting channel, showed as the scented substance transfer channel 753, where the plug 751 spans across the channel 753 except for the opening. The switch 750 includes a vertically-moveable piezoelectric component 752 that moves toward to cover and away to uncover the opening of the plug 701. For example, the component 752 can move based on a piezoelectric effect of the material(s) of component 752 in response to an applied electrical voltage from an electrical circuit. The piezoelectric component 752 can be configured as an expandable and contractible component including a compliant tip 754 attached to the end of the component 752 that makes contact with the plug 751 to cover the opening. For example the tip 754 can be made of PDMS.

For example, the exemplary piezoelectric actuator switching mechanism utilizes a switchable valve operation using a piezoelectric material in combination with tight-sealing tip material, e.g., such as PDMS or other suitable material. For example, an electrically activated piezoelectric valve for scent release on/off switching operations can be made with a horizontal movement valve design as shown in FIG. 7A or a vertical movement valve design as shown in FIG. 7B. The applied electric voltage can be supplied by a variety of electrical energy sources including wall plug-in electricity, a battery, a supercapacitor, solar cells, or other energy-providing devices. For example, the use of the mechanically compliant tip of the movable component can be used to provide improved reliability of scent release and blocking operations.

Scent Transport Enhancement Using Micro-Fan Array

In exemplary implementations of the device 100 including multiple transporting channels to selectively transport and dispense of scents (e.g., allowing for multiplexing control of switching for dispensing a desired scent to be released), the width or diameter of the odor release path may be reduced to accommodate many paths, in any desired configuration or bundle. Therefore, in such exemplary embodiments, the device 100 can include a fan-operated enhancement of scent transport including one or more miniature fans that can be installed in each of the scent transporting channels or a single fan connected to multiple channels. For example, as shown in FIG. 8A, a single-fan-sharing design embodiment can simplify the assembly and lower the fabrication cost of an exemplary FIGS. 8A and 8B show schematic illustrations of an exemplary single-fan and multi-fan enhanced operation of scent transport via a nano- or micro-scale channels in an exemplary multi-channel transporting channel array. The exemplary system can include an optional system in which pressurized, pumped, or fan assisted air at the inlet of system transports scented air through channels and outlet for scented gas delivery is also possible. For example, the dimension of the micro-fan can be in the range of 500-5,000 micrometers, preferably in the range of 1,000-5,000 micrometers.

As shown in FIG. 8A, a single fan configuration includes a plurality of subdivided or bundled channels (e.g., such as 40 channels), where the sub-channels can be configured to be nanoscale or microscale channels. For example, the sub-channels can be connected to each scent-generating chamber. In some configurations, the sub-channels can optionally include pure air/gas flow to merge with the scented substance at an outlet, e.g., for the purpose of dilution or variation or control of the scent intensity. The single-fan configuration of FIG. 8A (104) shows an optional air inlet(s) for dilution/scent intensity variation or control.

As shown in FIG. 8B, a multi-fan configuration includes a plurality of subdivided or bundled channels (e.g., such as 40 channels), where the sub-channels can be configured to be nanoscale or microscale channels, and one micro- or nano-fan is provided in each scent path. For example, the sub-channels can be connected to each scent-generating chamber. In some configurations, the sub-channels can optionally include pure air/gas flow to merge with the scented substance at an outlet, e.g., for the purpose of dilution or variation or control of the scent intensity.

Enhanced Ambient Temperature Scent Delivery without Using a Primary Heating Mechanism In order to enhance the efficiency and potency of odor/scent transport, especially using ambient scent delivery without using a heating mechanism (e.g., which provides a simplified device structure and lower cost), the disclosed technology includes the use of subdivided gas bubbles to enormously enhance the surface area of the overall bubbles. For identical volume of bubble, if the bubble size is subdivided, for example, from 2 mm diameter to 0.2 mm diameter bubblets, the surface area is increased by one hundredfold, thus significantly increasing the dissolution kinetics of scent gas into the cold air bubbles.

Several exemplary embodiments of ambient temperature scent delivery devices and mechanisms are described.

Figure 9:
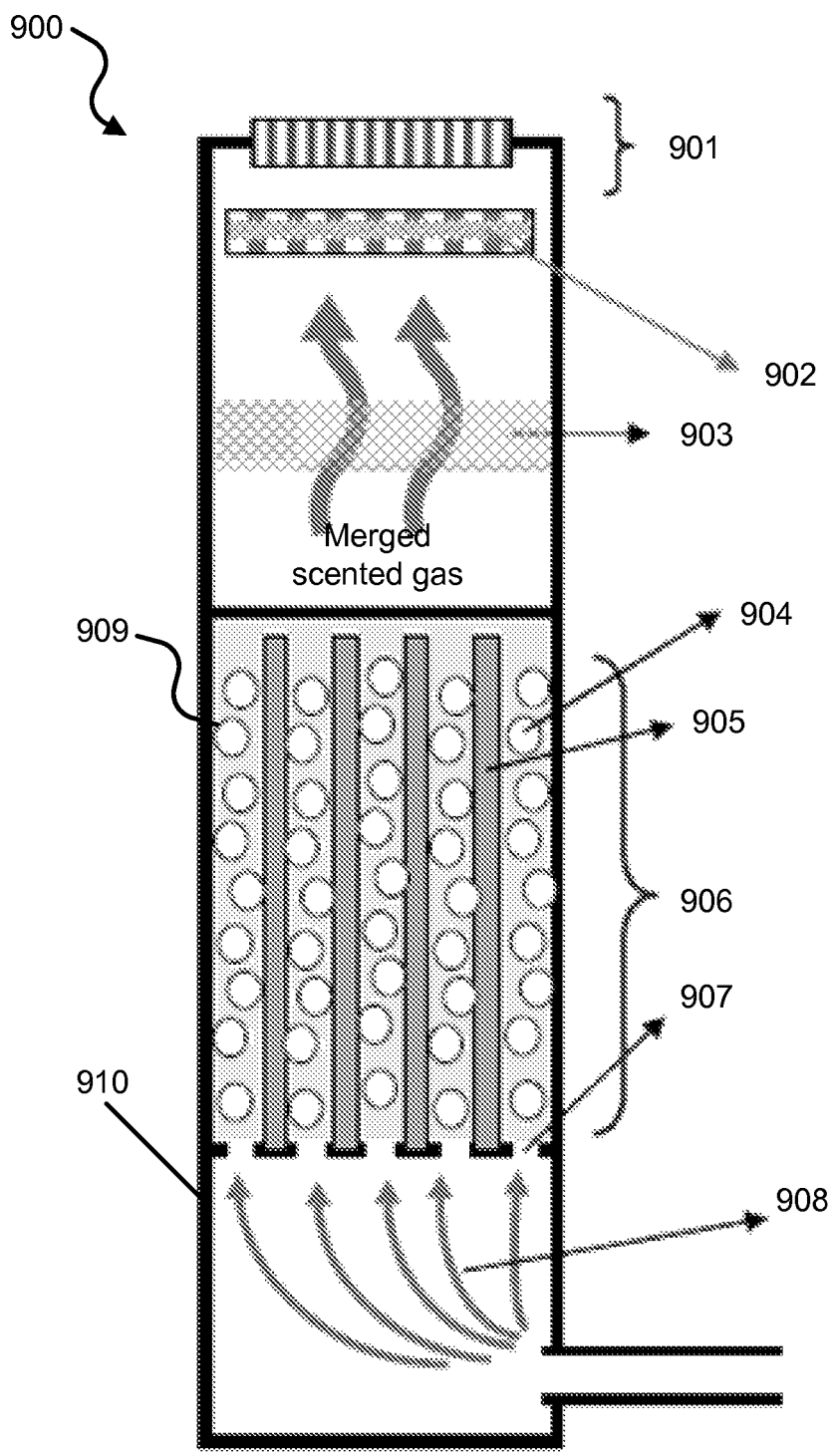
FIG. 9 shows a schematic illustration of an exemplary bubbling delivery mechanism of ambient temperature scented gas using subdivided micro-bubblets.

FIG. 9 shows a schematic illustration of an exemplary bubbling delivery mechanism 900 of ambient temperature (or optionally warmed) scented gas using a subdivided scent transport path through the cartridge storage compartment, which induces division of the bubbles into smaller microbubblets. In some implementations, for example, the ambient temperature scented gas for delivery can be optionally heated. The exemplary bubbling delivery of scented gas mechanism 900 can include an inlet region 908 for air blow into a channel or chamber 910 containing a subdivided scented liquid storage region 909 from which a scented gas is produced and controllably released from the channel or chamber 910.

The inlet region 908 of the mechanism 900 for air blow can include one or more inlets positioned in a variety of configurations in the inlet region 908. In some implementations, for example, a carbon filter or other type filter may be optionally included in the inlet region 908 for removal of impurities and unwanted organoleptic properties.

The subdivided scented liquid storage region 909 of the mechanism 900 can include a plurality of tiny holes or openings 907 to subdivide the air flow from the inlet region 908 but capillary hold the viscous scent liquid above the holes or openings 907 without leakage. The subdivided scented liquid storage region 909 can include the scent liquid storage chamber 906 (e.g., provided in a cartridge, such as the cartridge 120 that can be inserted into the device 100). The scent liquid storage chamber 906 can be continuously and/or continually refillable, or click-on, poke-ably or otherwise disposable or replaceable. The subdivided scented liquid storage region 909 can include scent-modifying structure formed of a sub-divider structure 905 of columns or walls, e.g., made of spaced-apart metal, ceramic or polymer columns, separated bundles, microwires and/or nano wires. For example, the sub-divider structure forms a subdivided path using nano- or micro-wires, ribbons, or other geometry or shaped elongated members, to produce a divided bubble structure for significantly increased surface area and enhanced scent molecular diffusion from a region of liquid to adjacent air (or gas) bubblets. Some examples of nanowire structures that can be implemented include silicon nanowires, ZnO nanowires, $TiO_2$ nanowires, metallic nanowires, and carbon nanotubes, e.g. produced by catalytic etching, hydrothermal synthesis, electrochemical etching or anodizing process, or chemical process, or chemical vapor deposition process. Exemplary microwire structures include bundled up microwires of metal, ceramic or polymers, e.g., preferably with a separator or bump structure added so that the microwires maintain certain gaps between adjacent microwire elements. The subdivided scented liquid storage region 909 can include smaller divided bubblets 904 that transport diffused scented gas through and out of the region 909.

The mechanism 900 can include a switchable gate 901 including an electrically switchable gate actuator, e.g., such as the magnetically actuatable latchable switch of the disclosed technology. Optionally, for example, the switchable gate 901 can provide introduction of added sensory elements or a cueing mechanism through presentation of variable air flow, change in temperature (e.g., heating) of scented air, sound, etc. Optionally, for example, the exemplary mechanism 900 can include a mist catching layer, filter or device 902. Optionally, for example, the exemplary mechanism 900 can include a filter 903 to capture impurities, e.g., such as a carbon filter or other type filter, which can be used to remove impurities and unwanted organoleptic properties.

Figure 10A:
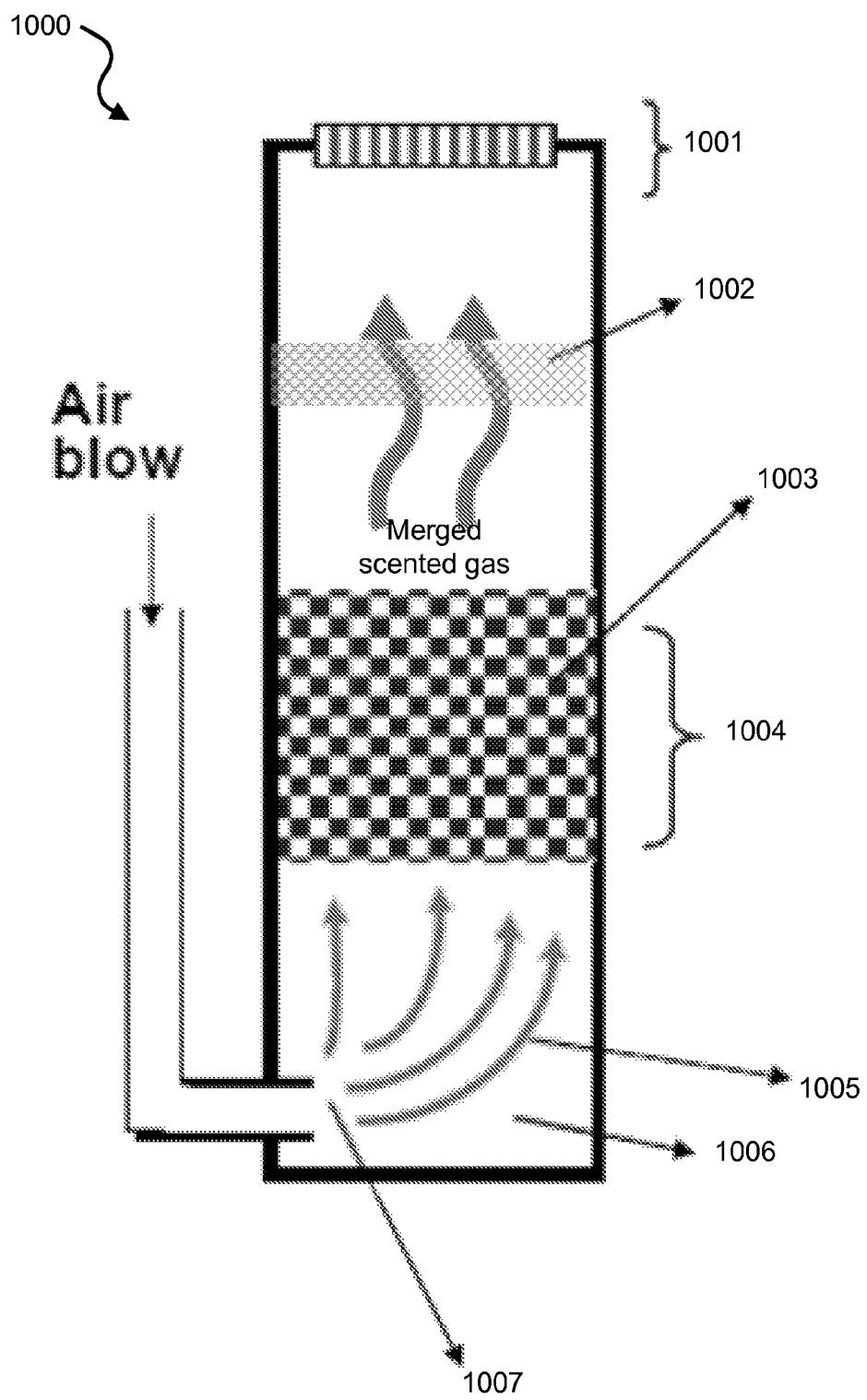
FIG. 10A shows a schematic illustration of an exemplary bubbling delivery mechanism of ambient temperature scented gas using porous structured paths.

FIG. 10A shows a schematic illustration of an exemplary bubbling delivery mechanism 1000 of ambient temperature scented gas using a highly porous material having porous structured paths. The mechanism 1000 can produce gas bubbles to produce a scent for release by passing air through the highly porous material. In some implementations, for example, the ambient temperature scented gas for delivery can be optionally heated.

The mechanism 1000 includes an inlet 1007 to allow air blow through tubes or via a one-way, free standing valve (e.g., in which the position of the inlet may be varied). The inlet 1007 can optionally include a carbon filer or other type filter for removal of impurities and unwanted organoleptic properties. The air blow from inlet region 1007 can enter a scent liquid storage chamber (e.g., provided in a cartridge, such as the cartridge 120 that can be inserted into the device 100). The scent liquid storage chamber 1006 can be continuously and/or continually refillable, or click-on, poke-ably or otherwise disposable or replaceable. As shown in FIG. 10A, air bubbles 1005 can go through the highly porous material 1004. The highly porous material 1004 can produce smaller divided bubblets 1003 through the pores. For example, the porous nano or microstructure can allow passage of liquid by air flow or capillary force, or gas (e.g., more efficient if heated).

The highly porous material 1004 can include, but is not limited to, nanoscale or microscale wire structures, nanoscale or microscale ribbon structures, nanoscale or microscale structures with nanopores or micropores, nanoscale or microscale particles, or nanoscale or microscale capsules. For example, the subdivided structure 1004 having porous, large-surface-area nano- or micro-paths (e.g., having ~100 nm to ~100 micrometer regime dimensions) can allow passage of liquid or gas (e.g., which can be enhanced if heated). Such materials can be configured to have a large surface area, and can have either a solid, immobile structure, a compliant movable structure of flexible wire/ribbon array, or can be an aggregate of loose particles or hollow capsules. For example, the porous large-surface-area material can be made of porous glass, porous alumina or any stable oxide, nitride, carbide, fluoride, metallic material or their combinations, e.g., such as made by sol-gel process, chemical synthesis, spark erosion, atomizing, plasma synthesis, mechanical pulverization, For example, the nano/micro particles can be loosely sintered to exhibit a large interconnected porosity, or a porous structure made by selective dissolution of second phase material from an initially multi-phase composites, anodization-induced, hydrothermally processed, thin film physical vapor deposition, chemical vapor deposition, electoless or electrochemical deposition and other porous structure fabrication approaches can all be utilized.

The mechanism 1000 includes a switchable gate 1001 including an electrically switchable gate actuator, e.g., such as the magnetically actuatable latchable switch of the disclosed technology. Optionally, for example, the mechanism 1000 can include sensory elements or a cueing mechanism, e.g., through presentation of variable air flow, change in temperature (e.g., heating) of scented air, sound, etc. Optionally, for example, the mechanism 1000 can include a filter 1002 to capture impurities, e.g., such as a carbon filter or other type filter, which can be used to remove impurities and unwanted organoleptic properties.

Figure 10B:
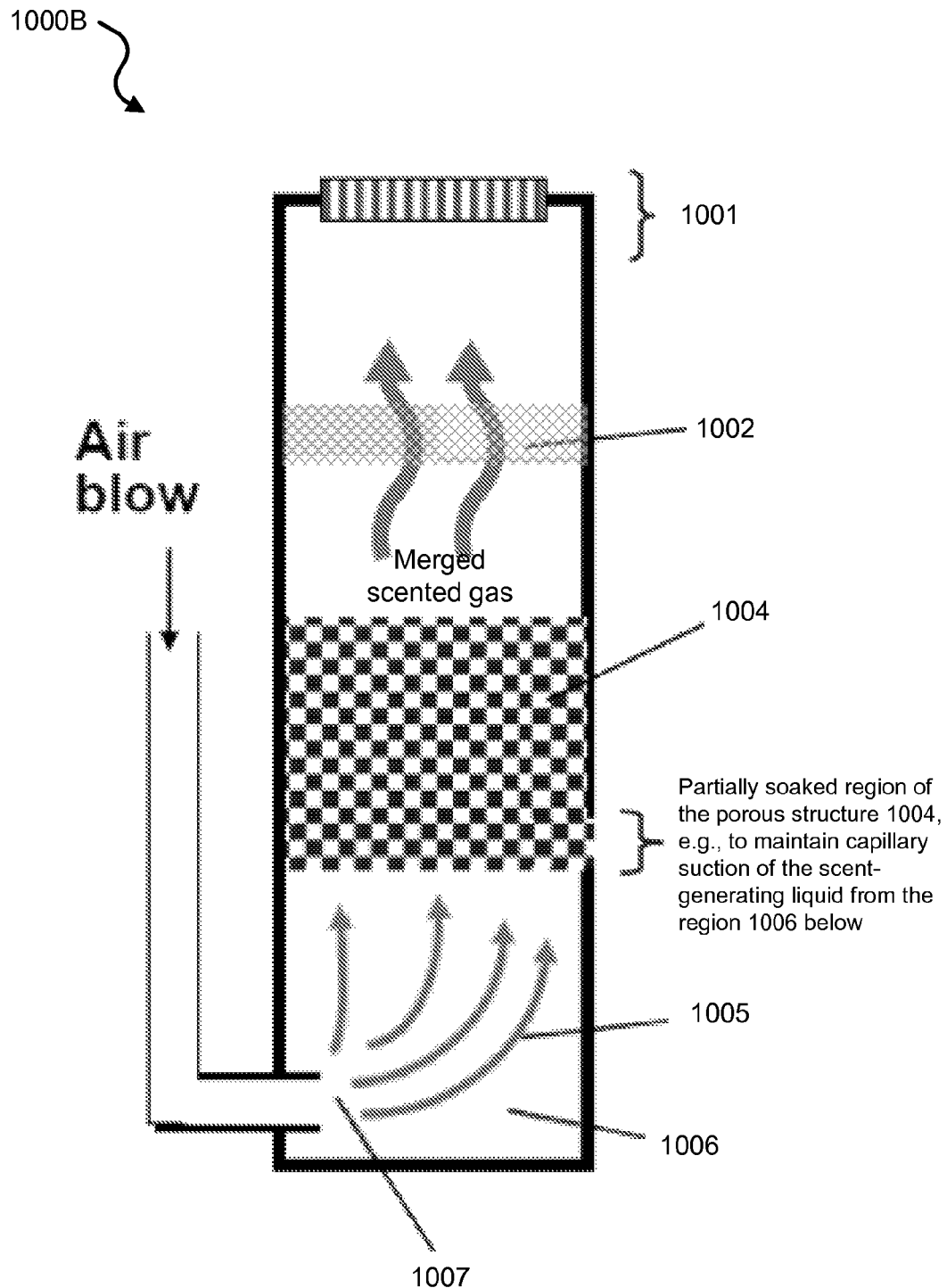
FIG. 10B shows a schematic illustration of an exemplary alternative embodiment of mechanism shown in FIG. 10A.

FIG. 10B shows a schematic illustration of an exemplary bubbling delivery mechanism 1000B, which is an alternative embodiment of mechanism 1000 shown in FIG. 10A. For example, the bottom portion of the highly porous structure 1004 is partially soaked with the scent-generating liquid from the scent liquid storage chamber 1006, so as to maintain some sustained capillary suction of the scent-generating liquid from the reservoir below and generate scent as the air flow is supplied.

Figure 10C:
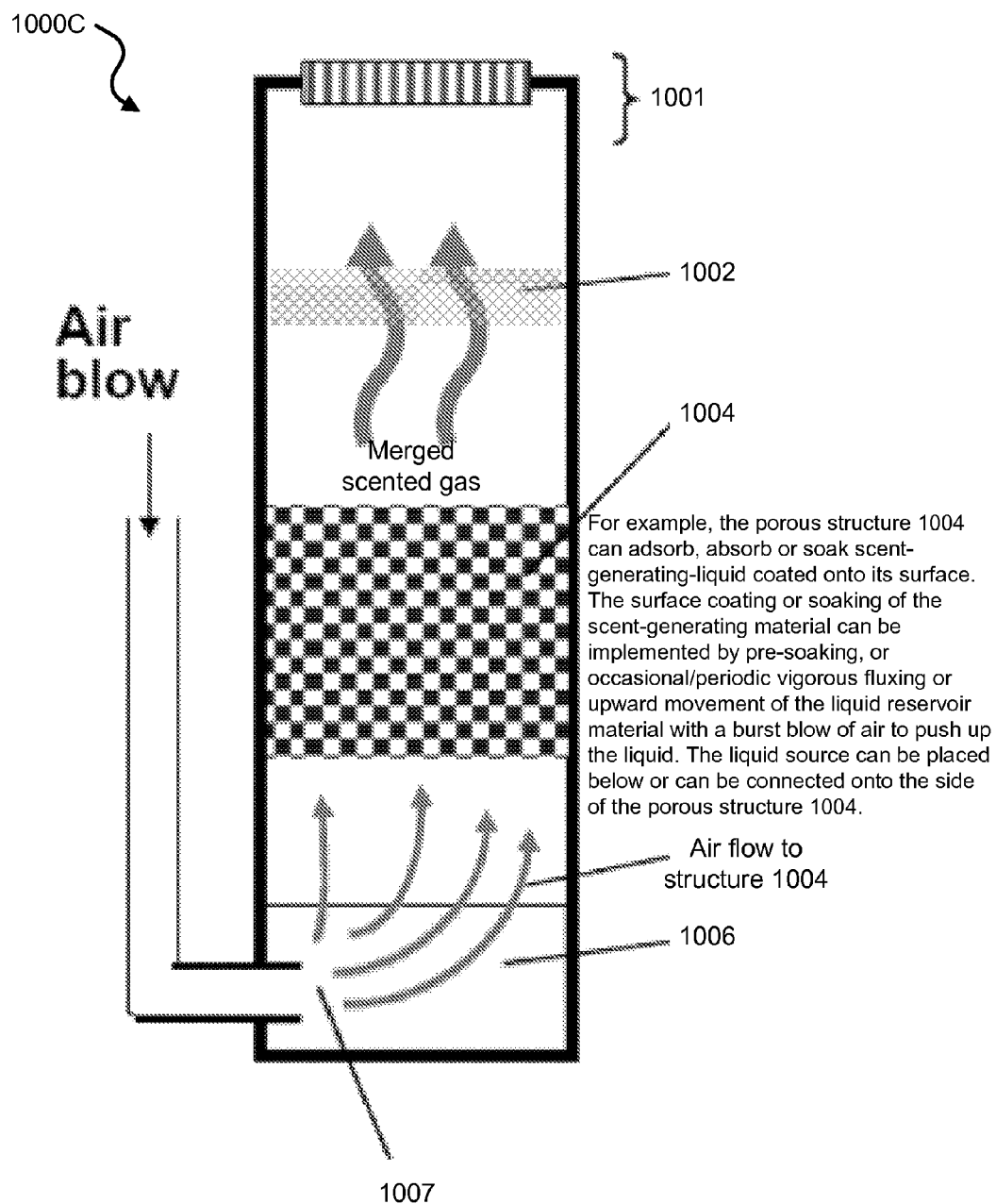
FIG. 10C shows a schematic illustration of an exemplary alternative embodiment of mechanism shown in FIG. 10A.

FIG. 10C shows a schematic illustration of an exemplary bubbling delivery mechanism 1000C, which is an alternative embodiment of mechanism 1000 shown in FIG. 10A. For example, the mechanism 100C is configured to utilize adsorbed, absorbed, or soaked scent-generating-liquid coated onto the surface of large-surface-area, porous nanostructures and/or microstructures of the highly porous material 1004. For example, the surface coating or soaking of the scent-generating material is arranged by pre-soaking, or occasional/periodic vigorous fluxing or upward movement of the liquid reservoir material with a burst blow of air to push up the liquid, or optionally, for example, may be replenished or fed by a wicking mechanism/structure between the liquid reservoir and the porous nano or micro structure. For example, an exemplary wicking structure can be made of metallic, ceramic, polymer, paper, cloth or carbon based materials, or composite structures comprising at least two of these materials.

Figure 10D:
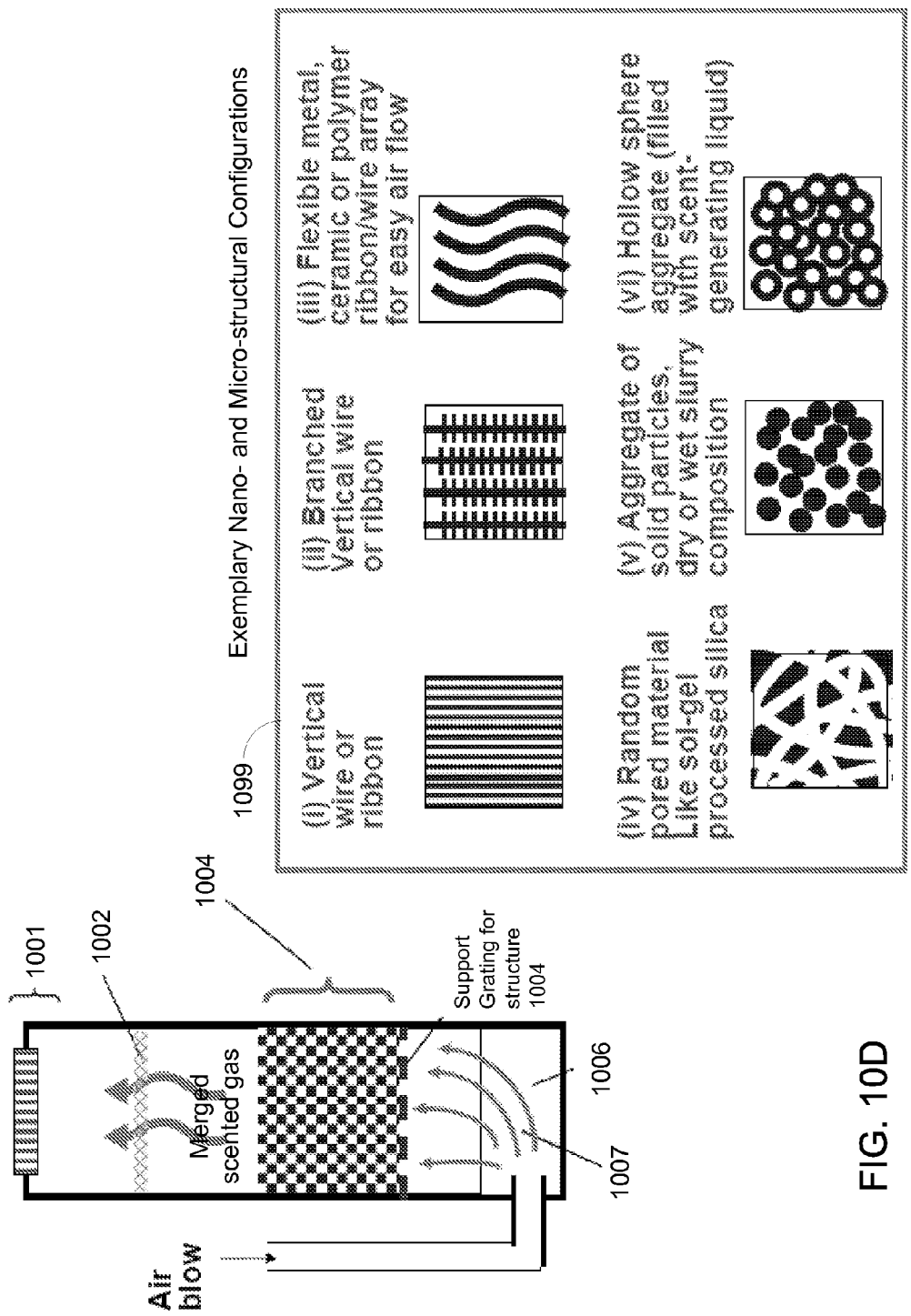
FIG. 10D shows a schematic illustration of an exemplary alternative embodiment of mechanism shown in FIG. 10A, and shows illustrative diagrams of exemplary highly porous structures including microstructure and/or nanostructure configurations.

FIG. 10D shows a schematic illustration of an exemplary bubbling delivery mechanism 1000D, which is an alternative embodiment of mechanism 1000 shown in FIG. 10A. FIG. 10D also an inset 1099 showing illustrative diagrams of exemplary highly porous structures including microstructure and/or nanostructure configurations. For example, the various exemplary structural configurations of porous nanostructures and/or microstructures having large surface area for surface-coating, -soaked or -impregnated the structure 1004 with scent-generating liquid.

As illustrated in FIG. 10D, the exemplary large-surface-area porous nano/micro structure 1004 can have various structural configurations with the large-surface-area surface coated or soaked or impregnated with a desired scent-generating liquid. Such configurations include, but are not limited to, i) vertically aligned and spaced-apart nano/micro wire or ribbons; ii) vertical wire or ribbon array with branched nanowires on each vertical wire stem; iii) flexible metal, ceramic or polymer ribbon/wire array that can be moved or bent sideways for easier air flow or liquid flow; iv) random pored material like sol-gel processed silica; v) aggregate of solid particles, dry or wet slurry composition; and vi) hollow sphere aggregate (e.g. filled with scent-generating liquid). Some example SEM micrographs of large-surface-area porous structures that can be useful for enhanced scent generation are shown in FIG.

Figure 10E:
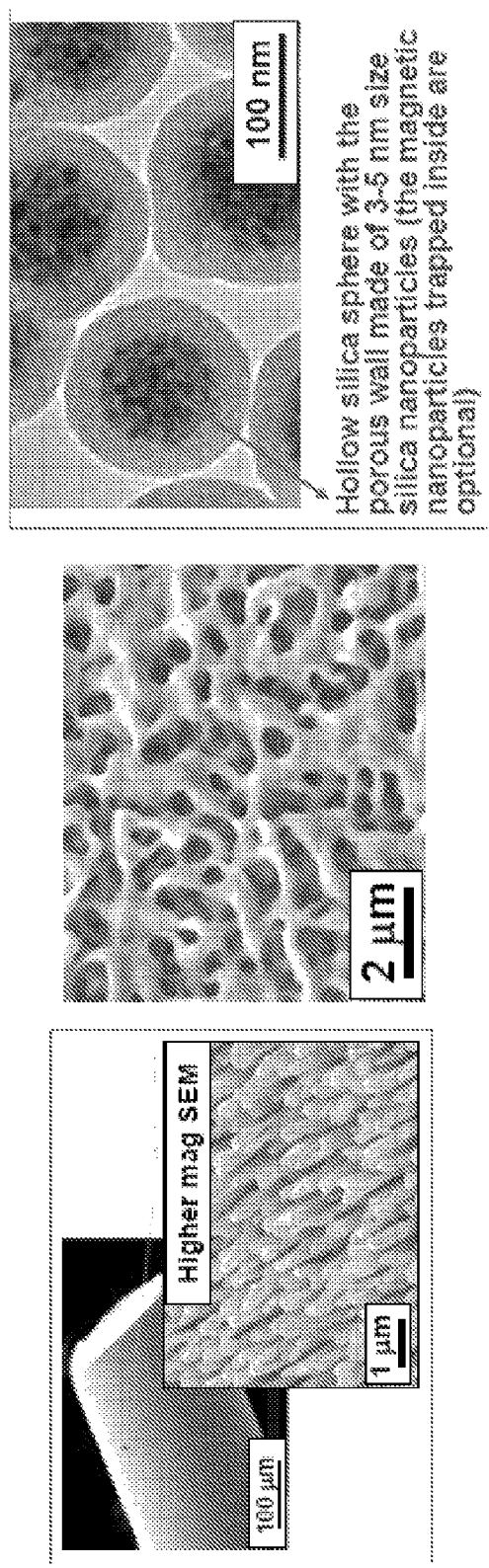
FIG. 10E show scanning electron micrograph (SEM) images of exemplary large-surface-area porous structures of the exemplary mechanisms of FIGS. 10A-10D.

FIG. 10E show scanning electron micrograph (SEM) images of exemplary large-surface-area porous structures of the exemplary mechanisms of FIGS. 10A-10D. The MP35N type stainless medical grade alloy wire (e.g., with a chemical composition of 35% Co-35% Ni-20% Cr-10% Mo in wt. %) can be subjected to ~13 MHz RF heating to a high temperature of several hundred degrees C., to perform plasma etch and introduce extremely fine, nanoscale branch nanowires for increased surface area, or is subjected to higher temperature plasma etch to introduce a highly porous, interconnected pore structure so as to surface decorate with scent-generating material coating.

Figure 11:
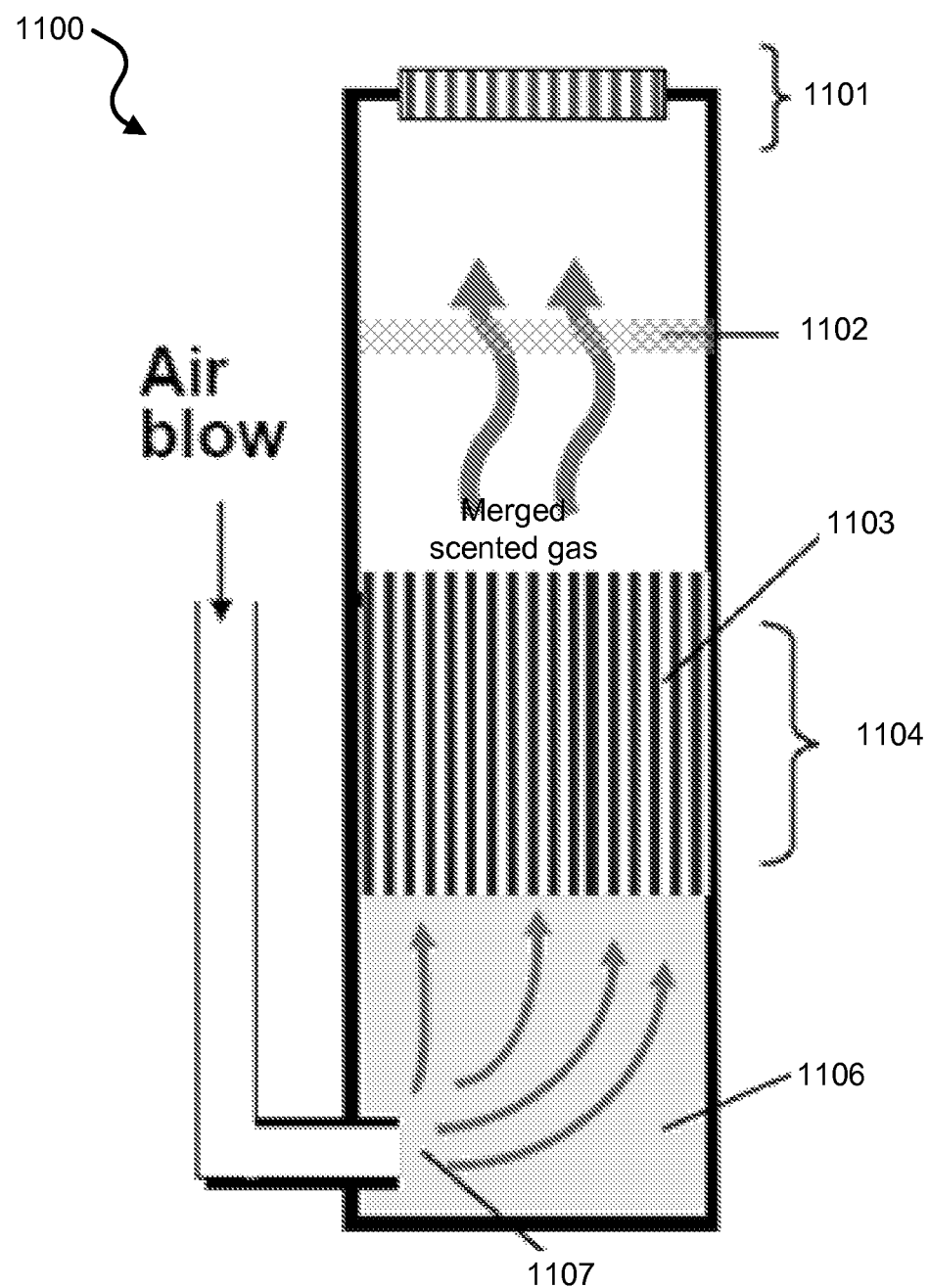
FIG. 11 shows a schematic illustration of an exemplary bubbling delivery mechanism of ambient temperature scented gas using vertically aligned porous paths.

FIG. 11 shows a schematic illustration of an exemplary bubbling delivery mechanism 1100 of ambient temperature scented gas using vertically aligned porous paths. The mechanism 1100 can include an inlet 1107 to allow air blow through tubes or via a one-way, free standing valve (e.g., in which the position of the inlet may be varied). For example, the air blow can be generated by pressurized air or fan-generated air or any single or mixed gases. The inlet 1107 can optionally include a carbon filer or other type filter for removal of impurities and unwanted organoleptic properties. The air blow can enter a scent liquid storage chamber 1106 (e.g., provided in a cartridge, such as the cartridge 120 that can be inserted into the device 100). The scent liquid storage chamber 1106 can be continuously and/or continually refillable, or click-on, poke-ably or otherwise disposable or replaceable. The mechanism 1100 includes a vertically-aligned porous material 1104 providing a porous path. The material 1104 can produce smaller divided bubblets 1103 through the pores. For example, the porous nano or microstructure can allow passage of liquid by air flow or capillary force, or gas (e.g., more efficient if heated).

For example, such materials can include vertically-aligned nanostructures or micropore structures such as made by anodized aluminum oxide (AAO) or titanium oxide nanotube array. The structure allows easier passage of liquid by air flow or capillary force, or gas (more efficient if heated). The exemplary vertically aligned porous paths structure 1104 can allow easier passage of liquid by air flow or capillary force, e.g., as compared to non-vertically aligned structures.

The mechanism 1100 can include a switchable gate 1101 including an electrically switchable gate actuator, e.g., such as the magnetically actuatable latchable switch of the disclosed technology. Optionally, for example, the mechanism 1100 can include sensory elements or a cueing mechanism, e.g., through presentation of variable air flow, change in temperature (e.g., heating) of scented air, sound, etc. Optionally, for example, the mechanism 1100 can include a filter 1102 to capture impurities, e.g., such as a carbon filter or other type filter, which can be used to remove impurities and unwanted organoleptic properties.

For example, it is noted that the transport of scented liquid or gas can be accelerated if optional heating is employed. Such optional heating can be employed in any of the exemplary mechanisms shown in FIGS. 9, 10A-10D, and 11.

Figure 12:
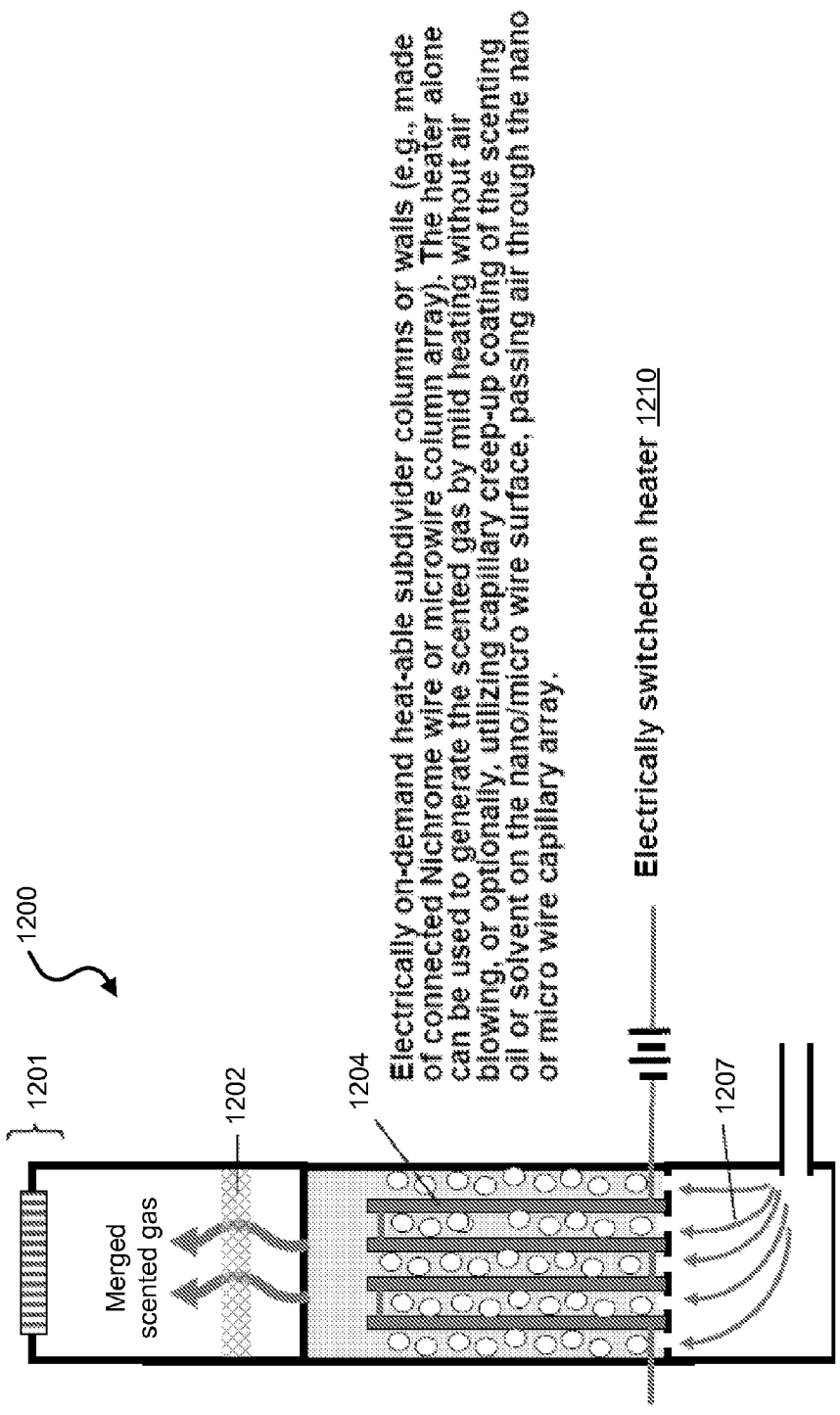
FIG. 12 shows a schematic illustration of an exemplary enhanced bubbling delivery mechanism of scented gas using electrically on-demand heat-able subdivider columns or walls.

FIG. 12 shows a schematic illustration of an exemplary enhanced bubbling delivery mechanism 1200 of scented gas using an exemplary electrically on-demand heat-able subdivider columns or walls (e.g., which can be made of connected Nichrome wire or microwire column array). Optionally, for example, the heater alone can be used to generate the scented gas by heating without air blowing, or optionally utilizing capillary creep-up coating of the scenting oil on the nano/micro wire surface, which is easily released by air blow even without heating The mechanism 1200 can include an inlet 1207 to allow air blow through tubes or via a one-way, free standing valve (e.g., in which the position of the inlet may be varied). For example, the air blow can be generated by pressurized air or fan-generated air or any single or mixed gases. The inlet 1207 can optionally include a carbon filer or other type filter for removal of impurities and unwanted organoleptic properties. The air blow can enter a region containing the electrically on-demand heat-able subdivider structure 1204 including microscale and/or nanoscale columns or walls. For example, the structure 1204 can be made of connected Nichrome wire or microwire column arrays. For example, the heater mechanism alone can be used to generate the scented gas by mild heating without air blowing, or optionally, by utilizing capillary creep-up coating of the scenting oil or solvent on the nano/micro wire surface, passing air through the nanowire and/or microwire capillary array. The mechanism 1200 can include a switchable gate 1201 including an electrically switchable gate actuator, e.g., such as the magnetically actuatable latchable switch of the disclosed technology. Optionally, for example, the mechanism 1200 can include sensory elements or a cueing mechanism, e.g., through presentation of variable air flow, change in temperature (e.g., heating) of scented air, sound, etc. Optionally, for example, the mechanism 1200 can include a filter 1202 to capture impurities, e.g., such as a carbon filter or other type filter, which can be used to remove impurities and unwanted organoleptic properties.

For example, it is noted that mechanisms to add sensory elements through presentation of variable air flow, change in temperature (e.g., heating or cooling) of the scented air, generation of sound, etc. can be optionally added to the exemplary mechanisms shown in FIGS. 9, 10A-10D, 11, and 12. Also, for the exemplary mechanisms shown in FIGS. 9, 10A-10D, 11, and 12, carbon or other type filters can be optionally added to or around the air or gas inlet(s) and other chambers or channels in the device.

X-Y Matrix Switching for Scent Delivery Selection

The disclosed scent delivery devices can be configured to be capable of 'multiplexing' (e.g., implementing sequenced or timed delivery of many scents), from which any desired scent can be selected and dispensed in an automated and/or on-demand fashion. For a relatively small number of different scents (e.g., less than 50), each of the scent release chambers can be independently addressed by an on-off command mechanism. However, as the available total possible number of different scents increases in a multiplexing system, individual control becomes increasingly complicated and cumbersome (e.g., a multiplexing system of up to 10,000 different scent chambers). According to the disclosed technology, for example, an X-Y matrix operation incorporating the latchable magnetic scent release mechanism and other switching is described in FIGS. 13-18.

Figure 13:
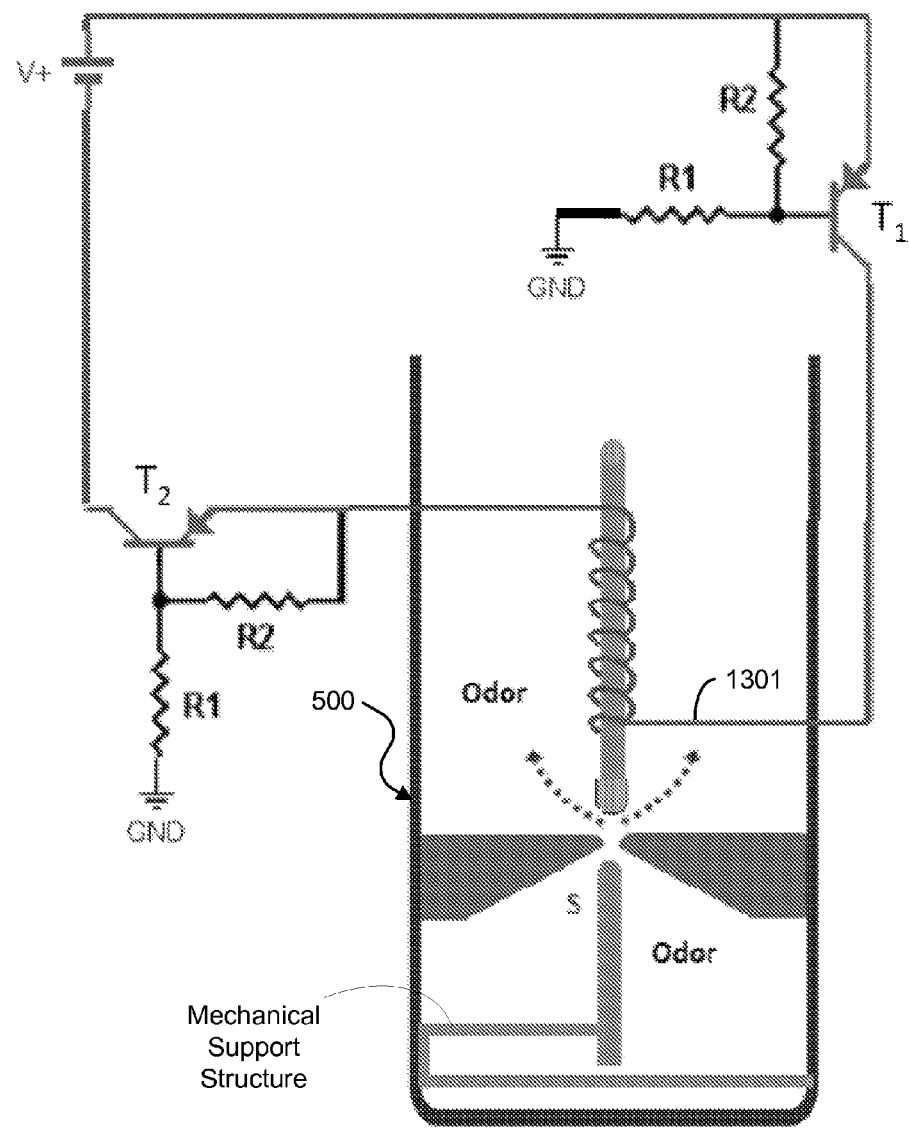
FIG. 13 shows an illustrative diagram of an exemplary magnetic latch that may be opened by demagnetizing the remanent magnetization in the core of the electromagnet using a transistor-based control circuit to control the application of the signal to cause actuation.

FIG. 13 shows a illustrative diagram of the exemplary magnetic latchable switch 500 that may be opened by demagnetizing the remanent magnetization in the core of the electromagnet using a transistor-based control circuit to control the application of the signal to cause actuation. As shown in the exemplary diagram of FIG. 13, both transistors T1 and T2 must be turned "on" for current to flow through the wire 1301 wound around the core and for the latch to open allowing the odorant to escape. For example, if either transistor is in the "off" state current will not flow and the latch will remain sealed. The scented substance (e.g., gas odor) can be loaded into the lower chamber and subject to pressurized, pumped, or fan-assisted air. This scented air cannot escape the chamber so long as the magnetic latch remains closed due to remanent magnetization of the electromagnets core. For example, once both transistors are turned on by grounding the otherwise open circuit connected to the base (e.g., a transistor switch setup), current is allowed to flow through the circuit, including the solenoid to operate with the doubled current (e.g., equivalent to $H_2$ field in FIG. 4) to induce the magnetic switching and the scent gate open or close activation. If the electric current equivalent to the magnetic field strength $H_1$ is applied (e.g., without combining the X-current and Y-current), the field strength is not sufficient to activate the core of the solenoid to magnetically switch. A gradually diminishing field cycle may then be used to demagnetize the core and open the latch. To close the latch again, a pulse current can be applied and then removed leaving remanent magnetization behind to hold the latch closed.

Figure 14A:
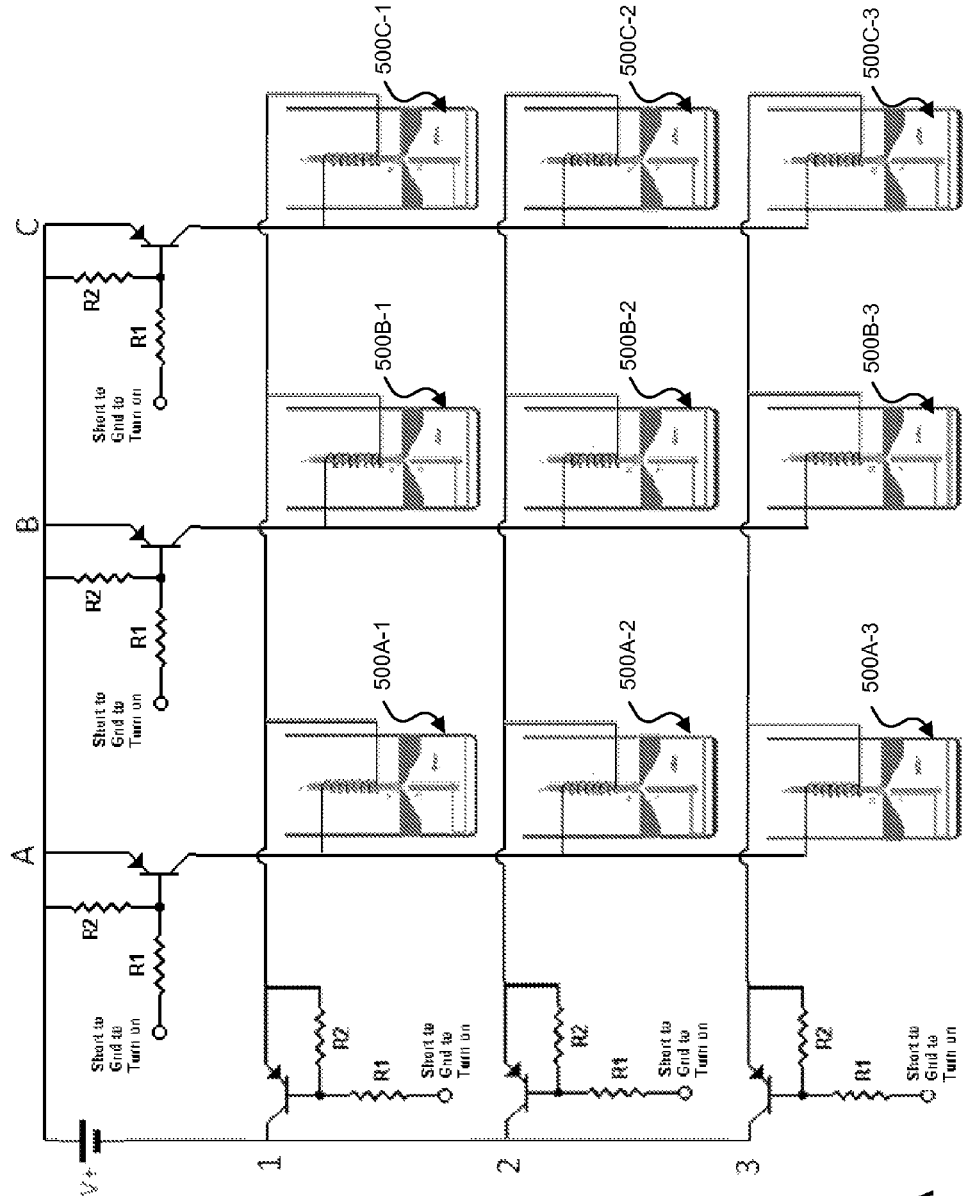
FIG. 14A shows an illustrative diagram of an exemplary 3×3 matrix of magnetic latches and transistors in a transistor-based control circuit for controlling the row and column of a selected latch.

FIG. 14A shows a schematic of an exemplary 3×3 matrix of magnetic latches and transistors in a transistor-based control circuit for controlling the row and column of a selected latch. For example, the transistors may be turned on by shorting the corresponding open connection to ground. For instance, if the exemplary transistor 1 and the transistor B were shorted, then the exemplary magnetically actuated latch 500B-1 would be actuated to open the channel and release the scented substance. This is just an example of one configuration of a transistor switch circuit for implementing the multiplexing of the disclosed scent delivery devices.

Figure 14B:
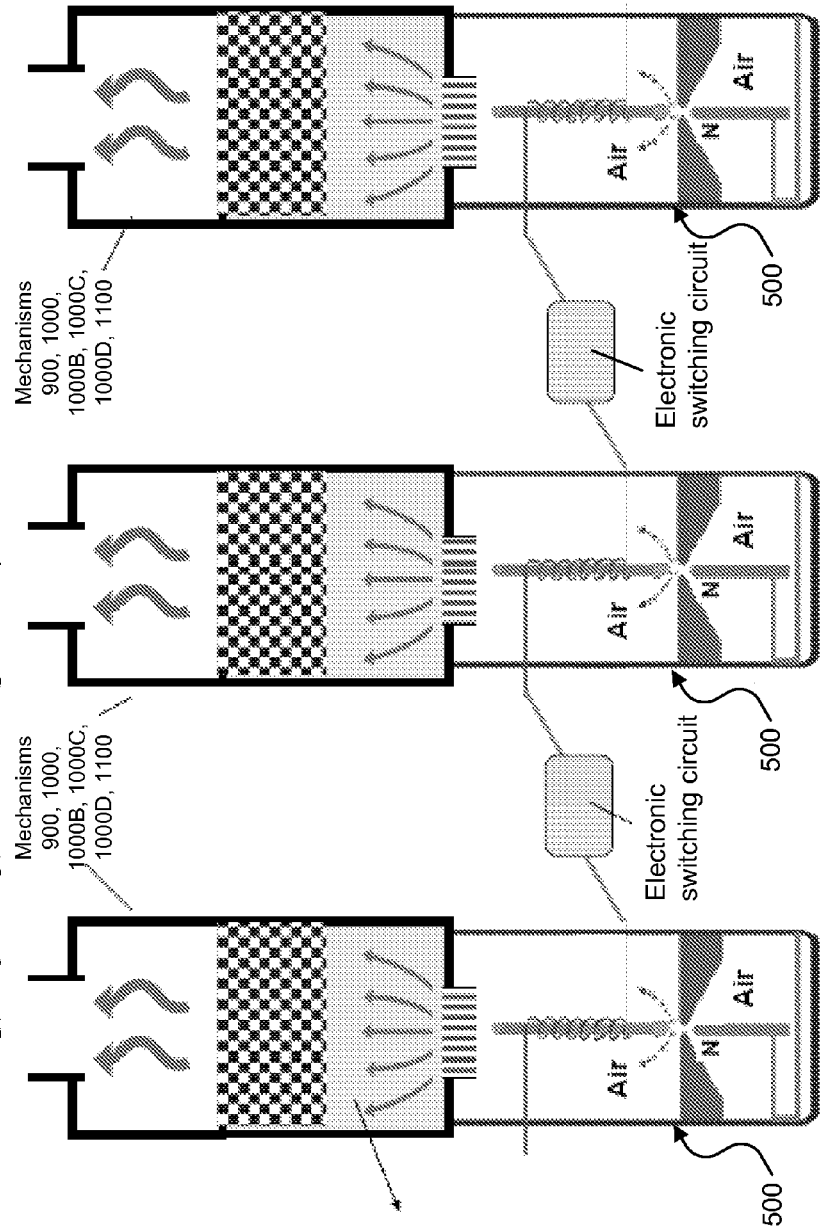
FIG. 14B shows an illustrative diagram of an exemplary magnetic gating array for air path switch-on/switch-off combined with an array of scent generation mechanisms corresponding to the air path.

FIG. 14B shows an illustrative diagram of an exemplary magnetic gating array for air path switch-on/switch-off combined with an array of scent generation mechanisms corresponding to the air path. For example, similarly as in the case of FIGS. 9, 10A-10D, and 11, different embodiments of the bubbling delivery mechanism can be utilized for scent generation in the exemplary gating array. For example, the source of the scent-generating liquid can be either a pool of liquid in a cartridge chamber, or adsorbed, absorbed or impregnated liquid inside or on the surface of the large-surface-area nano/micro structures, e.g., such as those illustrated in the inset 1099 of FIG. 10D and the exemplary SEM images of FIG. 10E. Also, the large-surface-area nano/micro structure for enhanced scent generation can be a fixed, immobile structure or a flexible/bendable structure, or a movable structure such as an aggregate of particles or hollow spheres, either loose, mostly in a dry configuration, or immersed in a scent-generating liquid. For example, the gating mechanism can also be selected from magnetically latchable device array, piezoelectric gating, thermal expansion gating or other devices.

Figure 15:
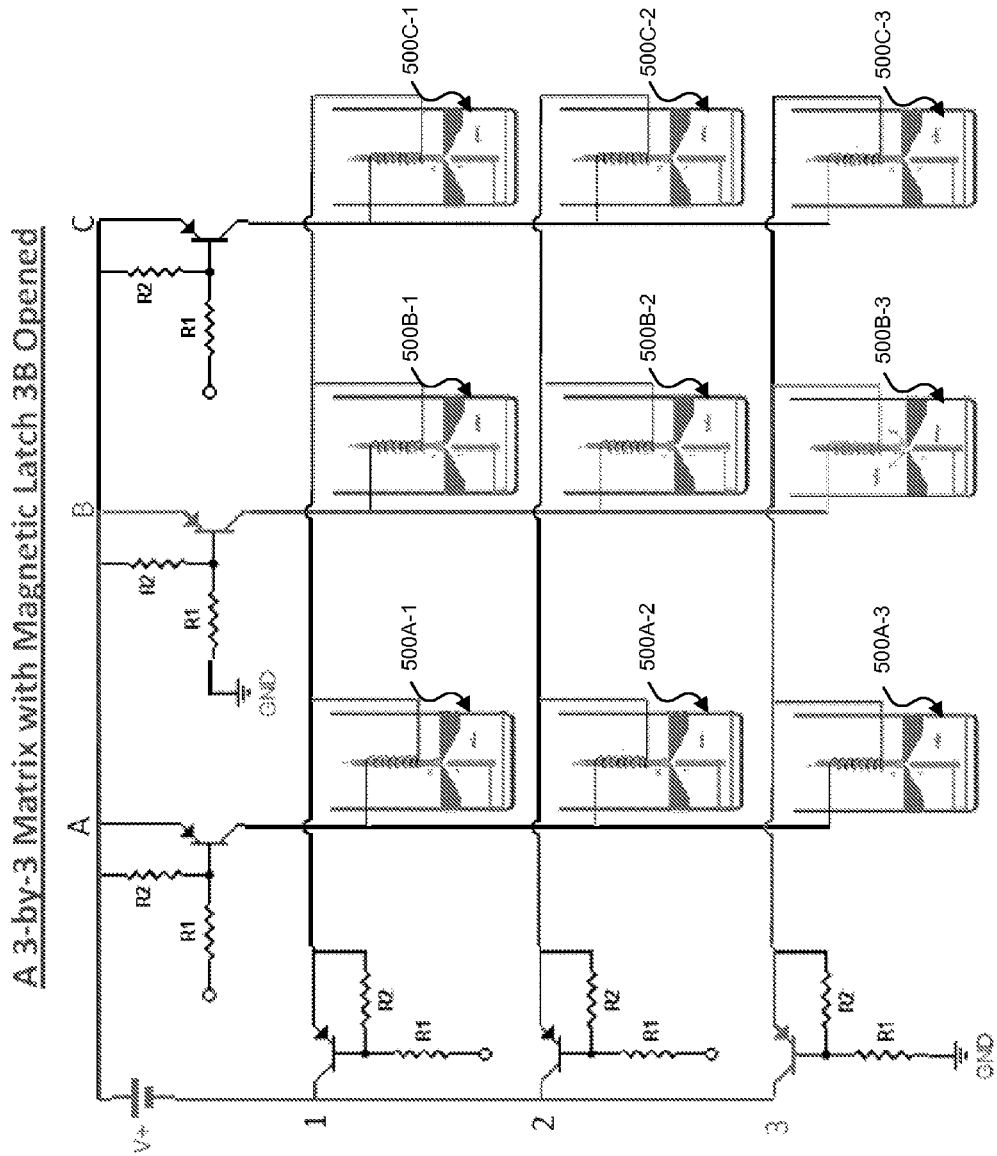
FIG. 15 shows an illustrative diagram of an exemplary 3×3 matrix of magnetic latches and transistors in a transistor-based control circuit for controlling the row and column of a selected latch, in which the magnetic latch of row 3, column B is activated.

FIG. 15 shows an illustrative diagram of an exemplary 3×3 matrix of magnetic latches and transistors in a transistor-based control circuit for controlling the row and column of a selected latch, in which the magnetic latch of row 3, column B is activated. In this example, by grounding the corresponding transistors, current is allowed to reach the latch 500B-3 and demagnetize the core resulting in an open pore for the scented substance to flow through. The remainder stay sealed.

Figure 16:
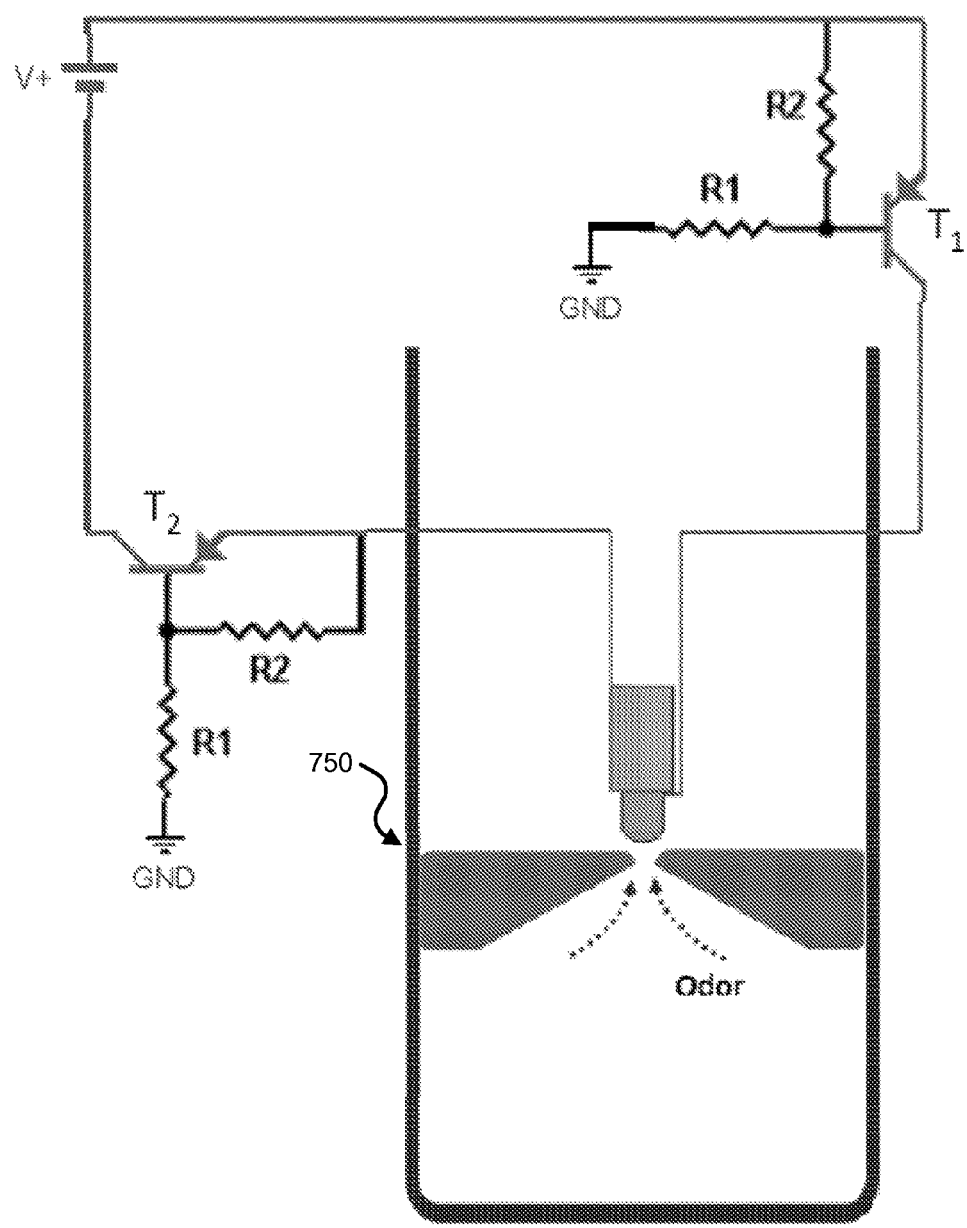
FIG. 16 shows an illustrative diagram of an exemplary piezoelectric actuated gating valve (e.g., a latch) which may be opened by applying a voltage to the piezoelectric actuator component that contracts as a result of an applied voltage.

FIG. 16 shows an illustrative diagram of an exemplary piezoelectric actuated gating valve (e.g., a latch) which may be opened by applying a voltage to the piezoelectric actuator component that contracts as a result of an applied voltage. For example, both transistors T1 and T2 must be turned "on" for sufficient voltage to be applied to the actuator to open the valve and allow the odorant to escape. If either transistor is in the "off" state, the voltage is insufficient to get the valve open and it will remain closed. For example, scented gas can be loaded into the lower chamber under compressed, fan assisted or pumped air. This scented gas cannot escape the chamber so long as the piezoelectric latch remains closed. For example, once both transistors are turned on by grounding the otherwise open circuit connected to the transistor base (e.g., a transistor switch setup), voltage is applied and current is allowed to flow through the circuit, including the actuator. The piezoelectric effect is contraction, thereby opening the pore and allowing scented gas to flow. For example, to close the valve again, either one or both of the transistors are turned off and voltage ceases to be applied and the current ceases to pass through the latch. The piezoelectric actuator returns to its original form and closes the orifice, ceasing airflow.

Figure 17:
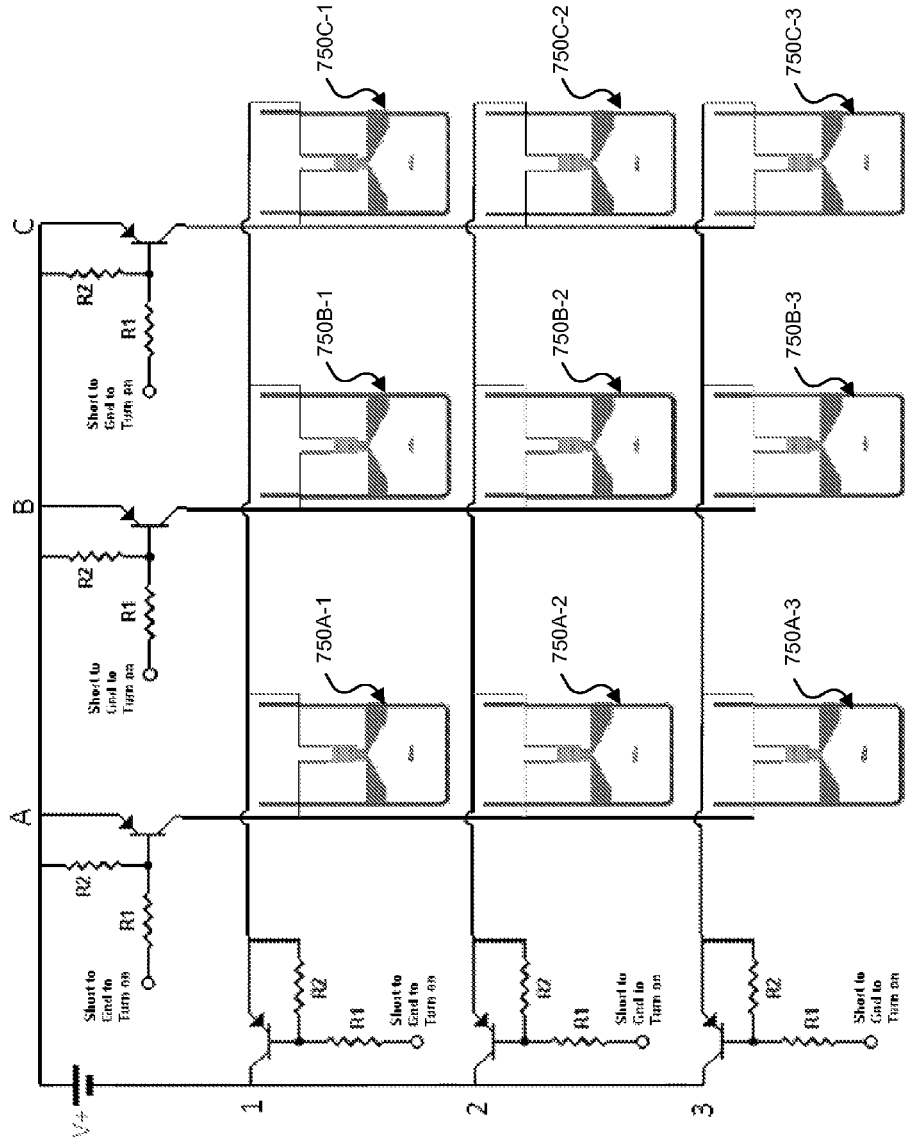
FIG. 17 shows a schematic of an exemplary 3×3 matrix of piezoelectric actuated gating valves (e.g., latches) with transistor in a transistor-based control circuit for controlling the row and column of a selected latch.

FIG. 17 shows a schematic of an exemplary 3×3 matrix of piezoelectric actuated gating valves (e.g., such as the exemplary piezoelectric actuated latchable valve 750) with transistor in a transistor-based control circuit for controlling the row and column of a selected latch. For example, transistors may be turned on by shorting the corresponding open connection to ground. This is just an example of one configuration of a transistor switch circuit for implementing the multiplexing of the disclosed scent delivery devices.

Figure 18:
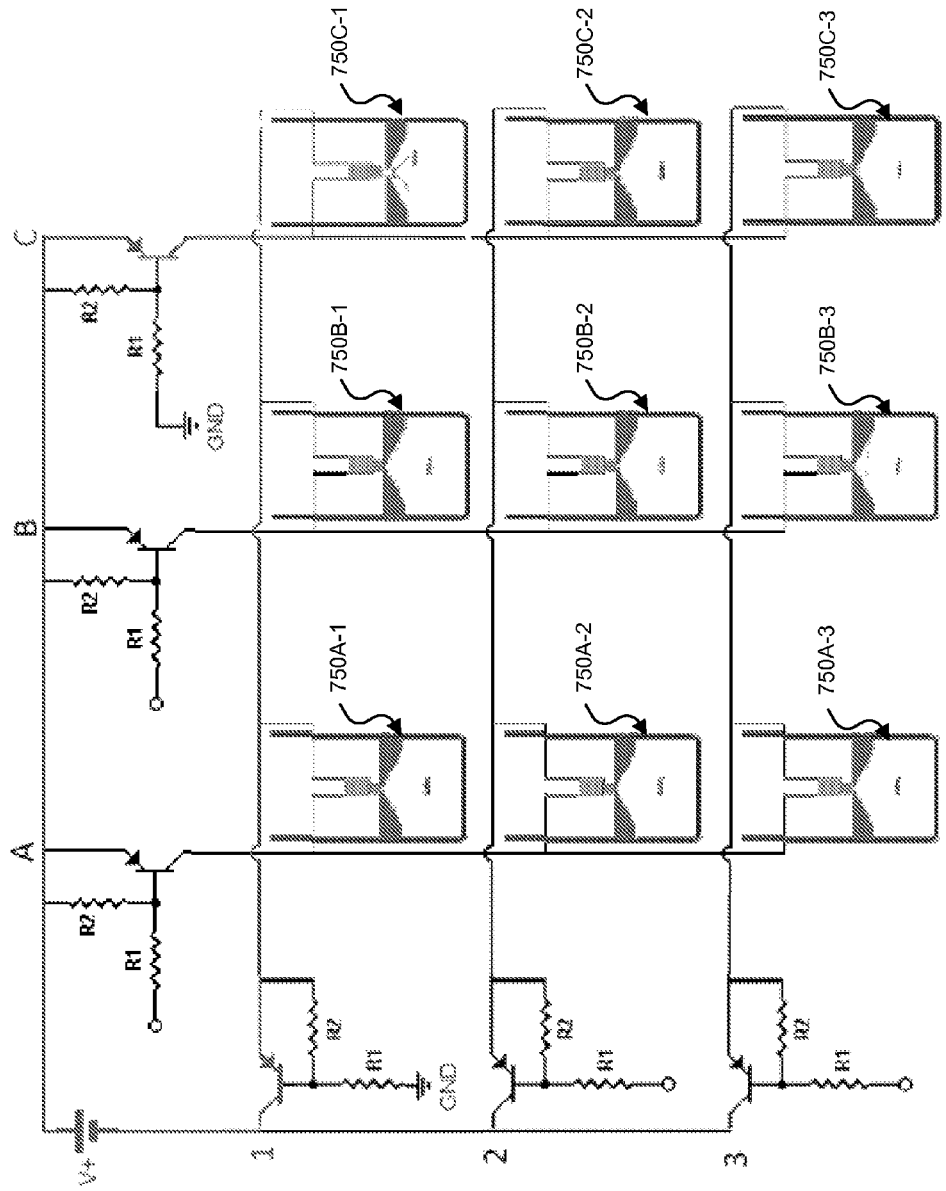
FIG. 18 shows a schematic of an exemplary 3×3 matrix of piezoelectric actuated gating valves (latches) and transistors in a transistor-based control circuit for controlling the row and column of a selected latch, in which the magnetic latch of row 1, column C is activated.

FIG. 18 shows a schematic of an exemplary 3×3 matrix of piezoelectric actuated gating valves (latches) and transistors in a transistor-based control circuit for controlling the row and column of a selected latch, in which the magnetic latch of row 1, column C is activated. For example, by grounding the corresponding transistors current is allowed to reach the latch and the piezoelectric actuator contracts resulting in an open pore for scented gas flow. The remainder stay sealed.

Figure 19:
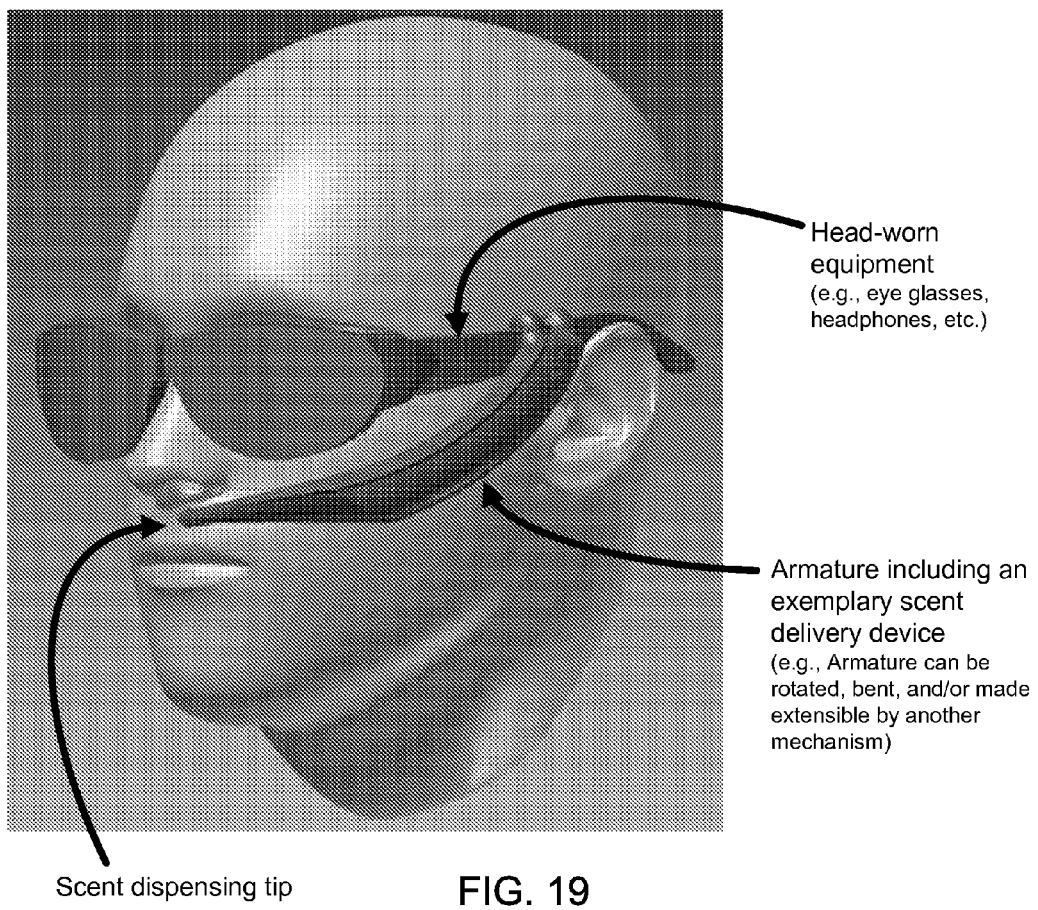
FIG. 19 shows an image illustrating, for example, that selected scents by an exemplary delivery device of the disclosed technology can be delivered on demand directionally into the headspace of the individual or at the nose directly using an armature type structure attachable or built into worn accessories such as eyeglasses, or via alternative embodiments or structures.

FIG. 19 shows an image illustrating, for example, that selected scents by an exemplary delivery device of the disclosed technology can be delivered on demand directionally into the headspace of the individual or at the nose directly using an armature type structure attachable or built into worn accessories such as eye glasses including Google glasses type of communication devices in form of eye glasses, music headphones or other head-worn equipment or pieces, or via alternative embodiments or structures. As illustrated in the example in FIG. 19, a scent delivery device is attached to at least one side of the eye glasses in form of an armature piece and includes an extension with a tip near the nose of the person for dispensing the desired vapor or liquid for the scent based on the scent release device designs disclosed in this document. The armature piece that embodies the scent deliver device may be movably engaged to the eye glasses to be rotated, bent, or adjustable in its tip position by the user. The armature piece may be folded or concealed at a different position when the scent deliver device is not used.

Figure 20:
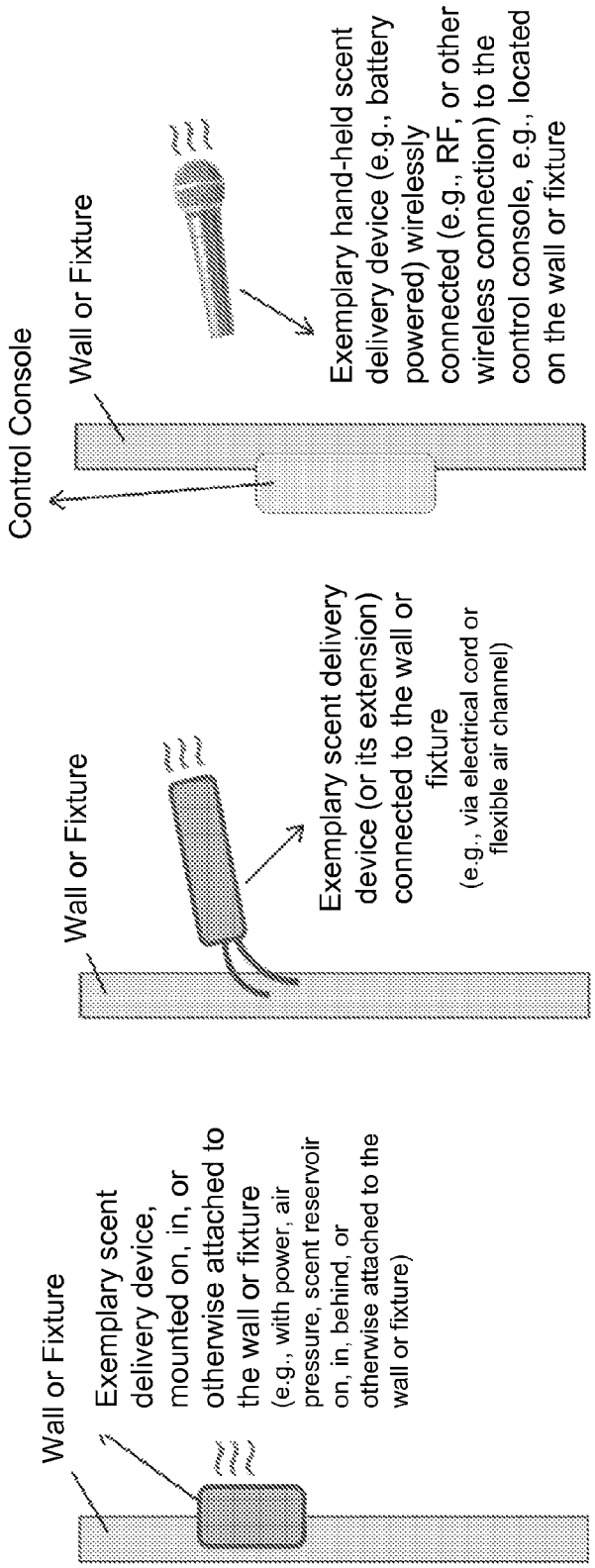
FIGS. 20A-20C show schematic illustrations of exemplary embodiments of a scent release device of the disclosed technology with respect to the building.

FIGS. 20A-20C show schematic illustrations of exemplary embodiments of a scent release device of the disclosed technology with respect to the building, vehicle, or furniture, or other structure. FIG. 20A shows an exemplary scent release device mounted on or in a wall or a fixture of the building, furniture, vehicle, etc. with the source of electrical power, air pressure, storage of scent reservoir array stored in, on or behind the wall or the fixture. FIG. 20B shows an exemplary scent release device extended by a cord or flexible air channel structure. FIG. 20C shows an exemplary scent release device operated as a completely separated hand-held device, (e.g., wand-like or microphone-like configuration), with the scent storage and possibly battery self-contained within the wand and are replaceable when needed. For example, the battery can be rechargeable by electrical connection or by AC proximity charging.

In some implementations, for example, the exemplary scent delivery device 100 can include one or more a scent gas or vapor diffusers at the opening end of the scent delivery device 100, e.g., near the end of a release tube, for control the spatial diffusion or spreading of the scented substance or scent. Such a scent diffuser may be configured to have a porous geometry, channeled or wire-array geometry, spiral array, or gas blocking or reflecting geometry. The scent diffuser component can be structured to have a geometry of tapered, perforated or spiral structure. The scent diffuser component can be configured as part of the housing 110 of the device 100. For example, in some implementations, the scent diffuser component is included as part of the transporting channels 115, e.g., to control the flow of the scented substance (e.g., vapor or gas) through the channels 115. Additionally, or alternatively, for example, the scent diffuser component can be attached to the housing 110 connected to the openings 113, e.g., to control the flow of the scent released from the device 100 to particular locations in the outside environment that enable the scent to remain in that desired location for a predetermined duration before dissipating.

Figure 21:
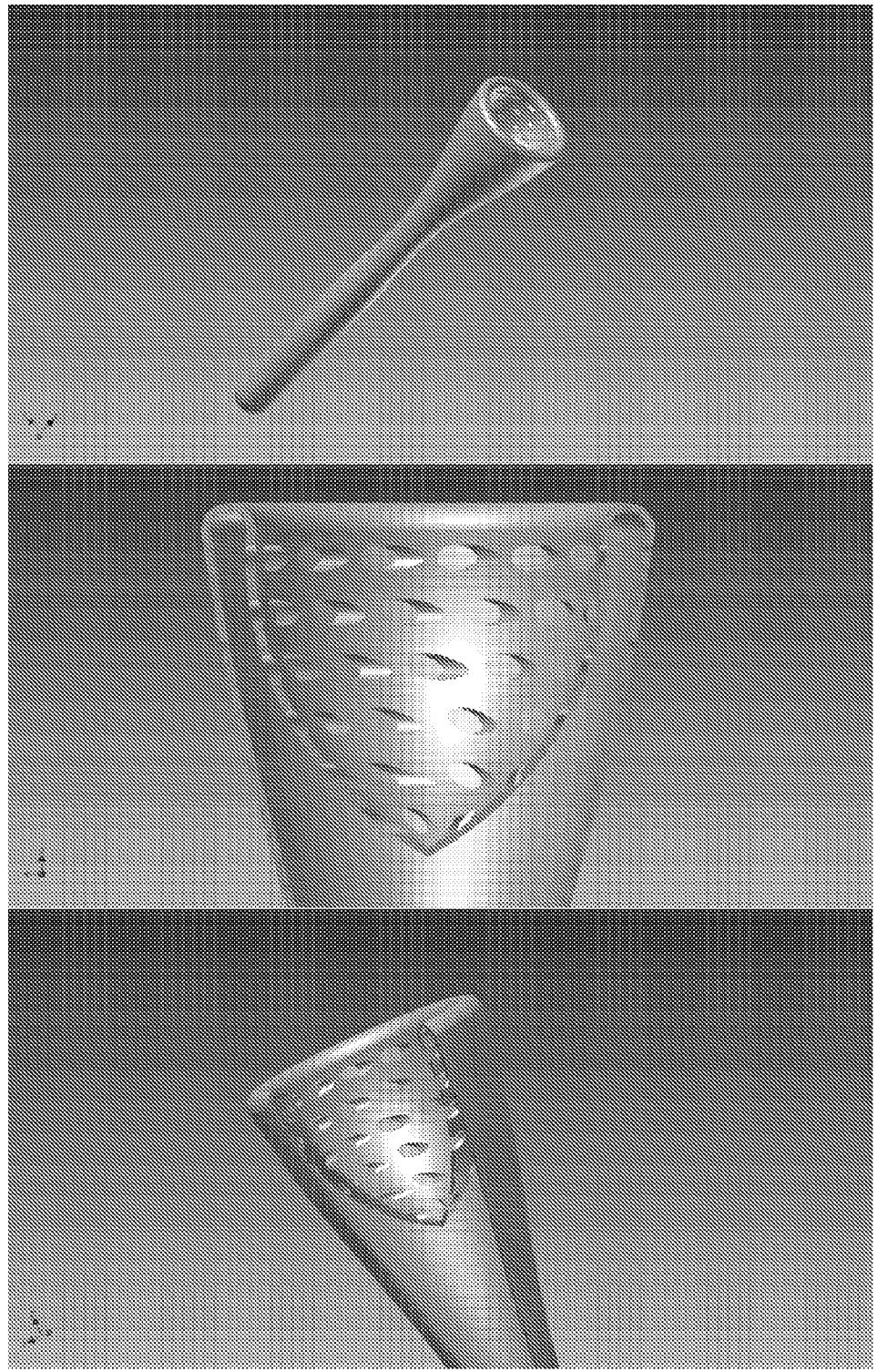
FIG. 21 shows schematic diagrams of an exemplary airstream diffuser cup or section of an exemplary scent release device.
Figure 22:
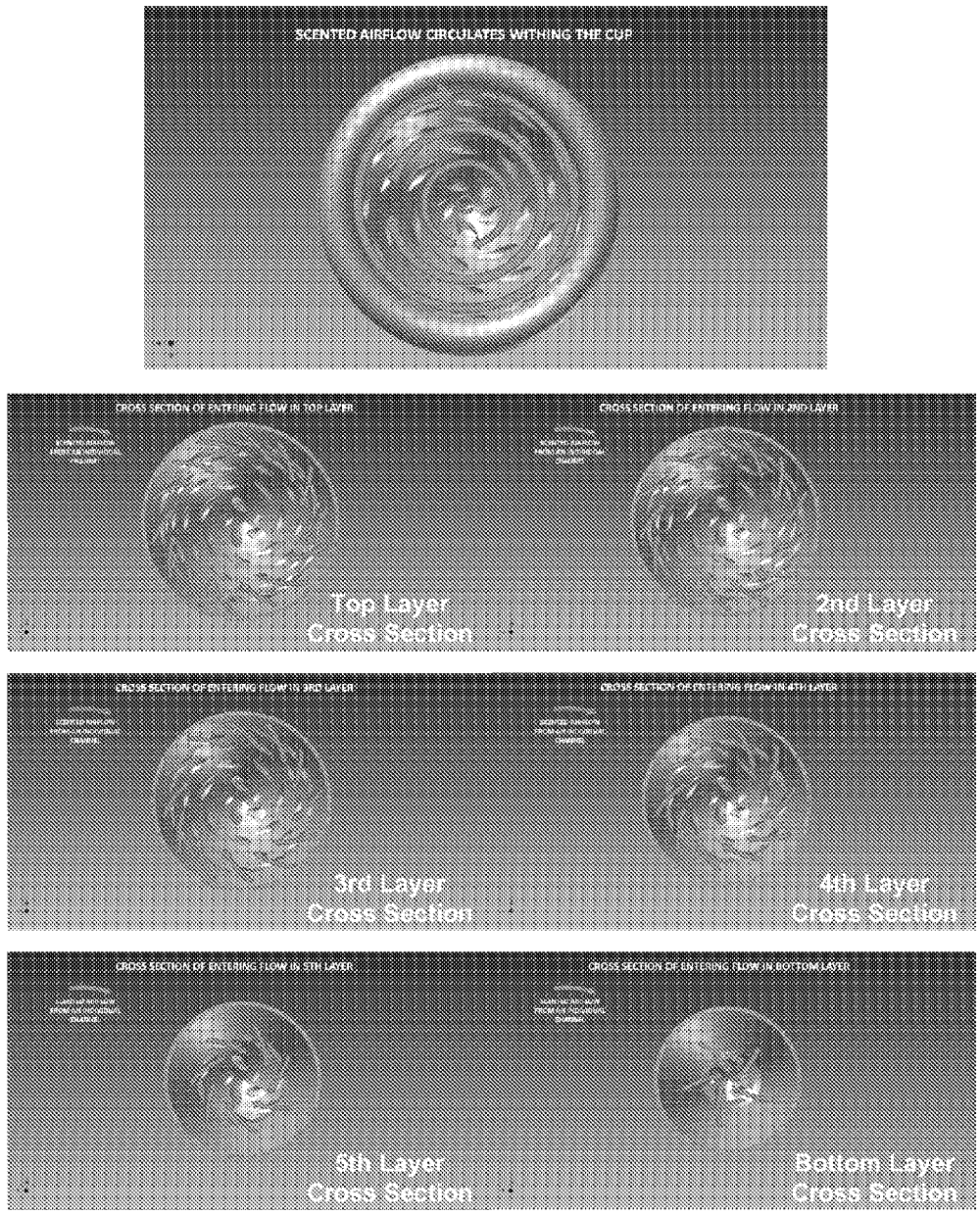
FIG. 22 shows a series of schematic diagrams illustrating scented airflow circulation within the exemplary airstream diffuser cup or section of the exemplary scent release device of FIG. 21.
Figure 23:
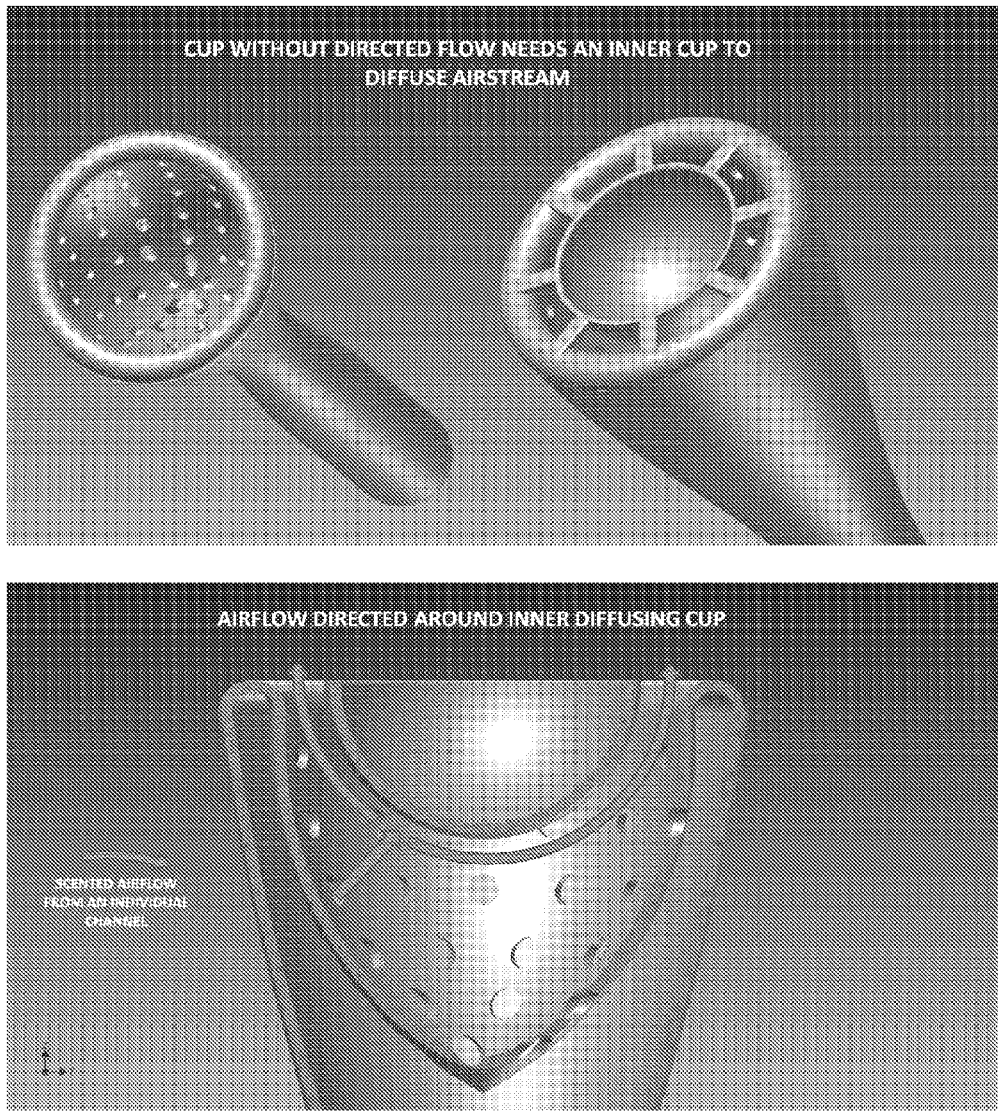
FIG. 23 shows schematic diagrams of an exemplary airstream diffuser cup or section of an exemplary scent release device including an inner cup.
Figure 24:
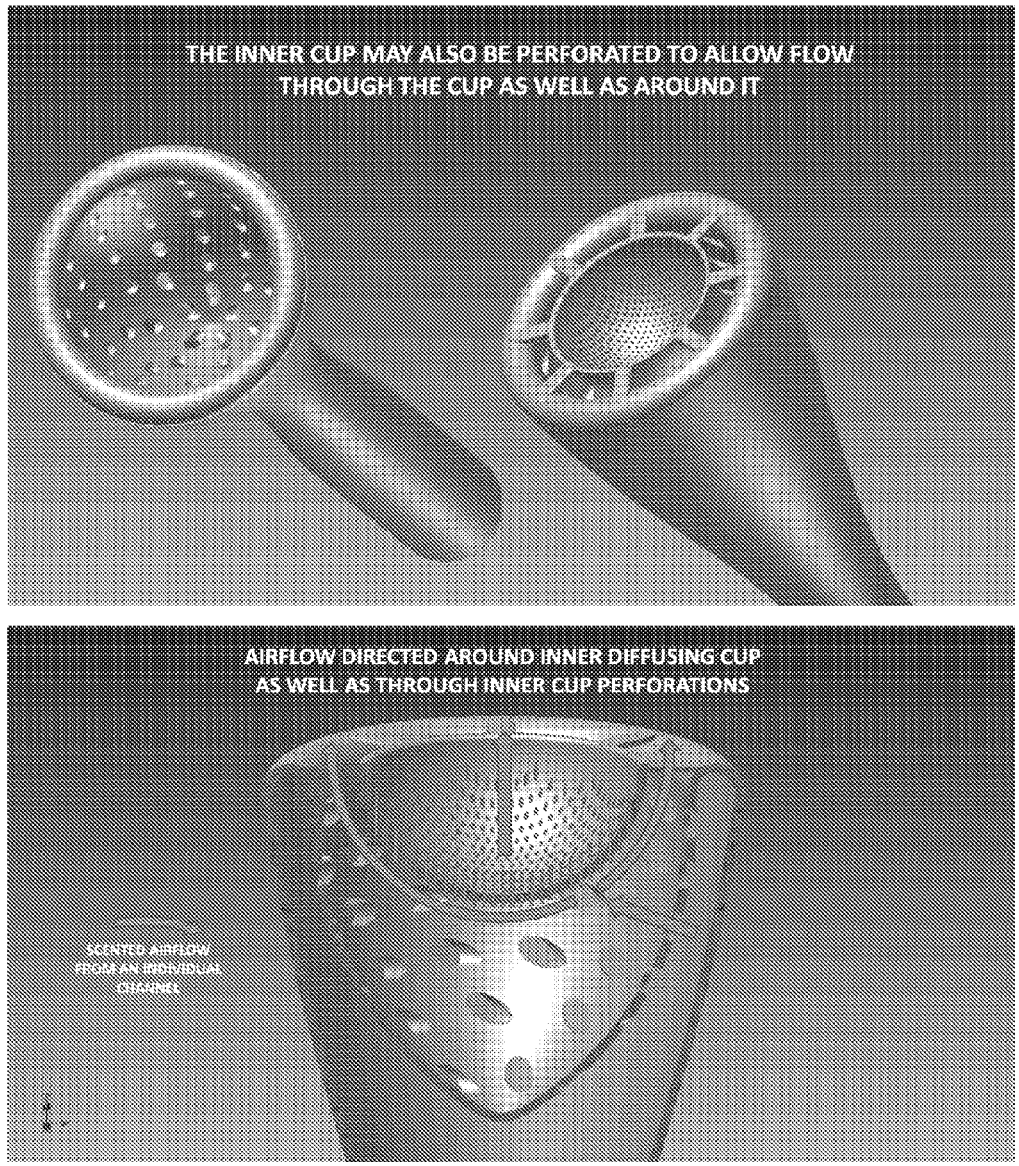
FIG. 24 shows schematic diagrams of an exemplary airstream diffuser cup or section of an exemplary scent release device including a perforated inner cup.
Figure 25:
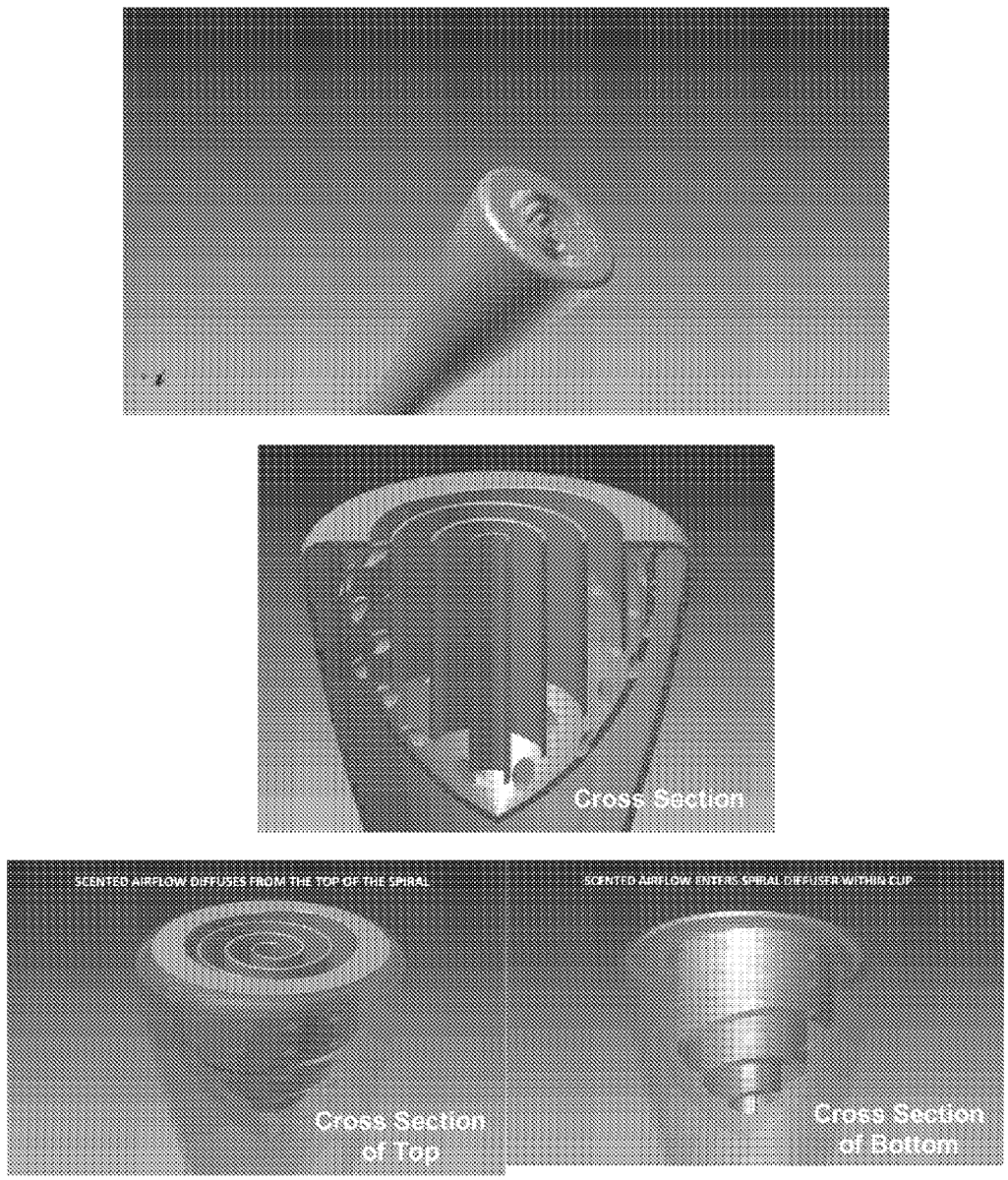
FIG. 25 shows schematic diagrams of an exemplary spiral-shaped airstream diffuser cup or section of an exemplary scent release device.

FIG. 21 shows schematic diagrams of an exemplary airstream diffuser cup or section of the exemplary scent delivery device. FIG. 22 shows a series of schematic diagrams illustrating scented airflow circulation within the exemplary airstream diffuser cup or section of the exemplary scent release device of FIG. 21. FIG. 23 shows schematic diagrams of an exemplary airstream diffuser cup or section of an exemplary scent release device including an inner cup. FIG. 24 shows schematic diagrams of an exemplary airstream diffuser cup or section of an exemplary scent release device including a perforated inner cup. FIG. 25 shows schematic diagrams of an exemplary spiral-shaped airstream diffuser cup or section of an exemplary scent release device.

It is to be understood that the above noted figures are for purposes of illustrating the concepts of the disclosed technology and may not be to scale. It is further understood that the present technology is not limited in its application to the details of construction and the arrangement of the components set forth in the accompanying figures and descriptions. The disclosed technology can be applicable to other embodiments or of can be practiced or carried out in various ways. It is also further understood that the phraseology and terminology employed herein is for the purpose of description and should not be regarded as limiting.

The disclosed scent generating devices can be used in conjunction with a variety of consumer product, industrial, civilian or military applications, including, but not limited to (a) entertainment such as motion pictures, animation, live theater, exhibitions, video games, presentations, and multi-media; (b) communications via cell phones or other communication devices; (c) gift device and gift-card electronics; (d) interactive or sensory books; (e) perfume sampling, development, and/or testing; (f) perfumes emitted through jewelry or other worn accessories; (g) localized air fresheners or fragrancing via or within furniture, furnishings, fixtures and appliances (h) scent-induced signaling or mapping; (i) training or testing; (j) education; (k) air fresheners in vehicles; (l) point of sale or augmented reality advertisement of foods, flowers, consumer goods and packaging; (m) biological, physiological or neurological activation/stimulation; (n) medical therapeutics and diagnosis; (p) malodor control and masking; (o) hygiene; (p) detoxification of harmful gas, (q) controlled, timed release of sleeping gas or unconsciousness-inducing gas, or laughing gas, (r) controlled, timed release of scents for behavioral control or influence of animals; and, (s) release of selective gases to influence and/or control the behavior of soldiers, etc.

According to the disclosed technology, for example, the scent generating device can be either fixed, portable, or (animal or human) body wearable. The size and design of the device and cartridge system that carries the scent generating liquid or material is adjusted accordingly depending on applications.

According to the disclosed technology, for example, the devices and mechanisms described herein are scalable to permit delivery of gas, e.g., scented or unscented, into larger (non-localized) spaces.

A number of embodiments of the disclosed technology have been described. Nevertheless, it will be understood that various modifications may be made without departing from the spirit and scope of the disclosed technology. Accordingly, other embodiments are within the scope of the following claims. For example, wireless or wired activation/deactivation or remote controller activation/deactivation can be incorporated to the scent-generating devices.

Also, in embodiments dispensing and delivering gases, one or more filters may be added for the purpose of removing impurities from the air in the incoming air, as well as near the outlet to remove impurities (and/or unwanted organoleptic properties in scented gas).

Furthermore, screened or otherwise displayed images can be synchronized, according to the disclosed technology, for example, with the release of scents using counted timing sequence, or coded activation utilizing pre-embedded electronic signals received by the scent-release device by wire or wireless technique, or by using the displayed image (or components thereof) itself as the signal that can be detected by the scent-release device.

Another variation in the exemplary device is for applications for desktop computers, cell phones, tablets, wearable devices, and/or laptop computers, in which the scent-releasing device, according to the disclosed technology, is connected to the main cell phone, write-pad or computer host device through the USB port, speaker jack outlet, other ports or wireless or remote mechanisms, with the scent-release device comprising an array of one-time-usable, replaceable or refillable cartridge that stores the scenting liquid or material, a component that allows selective passage of scented gas or vapor or mist or liquid in the multitude of path arrays, and electronically activated switch array that allows selection of specific scent to be passed.

Yet another variation is to incorporate a coding/signaling system that allows synchronization of the scent release timing with the exact moment for the corresponding displayed image or voice mail message or written message, and other control and powering device components, optionally combined with various memory technologies or devices, audio, visual or audiovisual technologies or devices and other sensory technologies and devices (haptics, etc.). According to the disclosed technology, the coding mechanism to synchronize the displayed image (or other virtual reality actions such as sound, music, mechanical vibration, etc.) with the corresponding scent release can be based on image recognition, voice recognition or other biometrics, electronic timing recognition, motion, light and/or color sensors, as well as by utilizing hidden image, sound, electronic or wireless signals from the scenes displayed (whether on screen or via other display mechanism) that can be recognized/detected by the scent-releasing device to initiate or stop release of specific scent(s).

In some aspects, the disclosed technology can include the following devices, systems, and methods.

In one example, the disclosed technology includes a single or multiple path gas, vapor or liquid dispensing and delivery device including one or more liquids or scented compositions or materials stored in one or more chambers encased in or as part of disposable, re-fillable or replaceable cartridges. The exemplary device can include single or multiple gas, vapor or liquid transporting paths. The exemplary device can accelerate the speed of (scented or unscented) gas, vapor or liquid movement. The exemplary device can include methods of switching ON or OFF each of the multiple paths to selectively allow passage of a specific gas, vapor or liquid. For example, such scent generating devices can be either fixed, handheld, portable or wearable (e.g., attachable to wearable accessories such as eyeglasses (e.g., including eye glasses with display and communication capabilities such as Google glasses) or music headphones). For example, such scent generating devices can, in part or whole optionally disposable, be extensible or adjustable to accommodate optimal placement within, or directed at, a headspace. For example, such scent generating devices can be used for micro- or nano-fluidic or gas control or timed release and delivery.

In some examples, the exemplary device can include: magnetically latchable gating structures with at least one solenoid and at least two mating magnetic materials incorporated, with at least one magnetic material as a solenoid core having an essentially square-loop magnetization loop having a coercive force of preferably at least 20 Oe but preferably less than 100 Oe, with the squareness of the loop desirably at least 0.85, preferably at least 0.9, more preferably at least 0.95, as described in drawings of FIGS. 1-5 with detailed descriptions in the specification, e.g., with at least one of the magnetic elements bending or position changing upon magnetic field application to the surrounding solenoid to activate the closure or opening of a path orifice for transport of a gas, vapor or liquid.

In some examples, the exemplary ON-OFF gate opening switching can be accomplished with a pulse current of preferably less than 1 second, with the ON or OFF state maintained without any use of electrical power once the switching is done.

In some examples, the exemplary ON-OFF gate opening switching can be accomplished by a short, preferably less than 1 second AC magnetic field with a gradually diminishing amplitude for demagnetization.

In some examples, the exemplary solenoid with a magnetic core can be positioned vertically or horizontally, and the tip of the moving part can be coated with a compliant, elastometic or other material for tight sealing when the switch is closed.

In some examples, the exemplary ON-OFF gating of the single or multiple channel devices can be enabled by controlled thermal expansion of spring material and compliant, tight-sealable elastomeric or other pliable material, with such ON-OFF gating being either non-latchable or latchable.

In some examples, the exemplary ON-OFF gating of the single or multiple channel devices can be enabled by controlled expansion, bending of shape-change of piezoelectric materials that show an dimensional expansion upon a voltage application.

In some examples, the exemplary gating switching ON-OFF in an X-Y matrix array can be enabled by transistor or relay switch array.

In some examples, the exemplary gating switching ON-OFF in an X-Y matrix array can be enabled by magnetically latchable switch using square loop magnetic core inside a solenoid.

In some examples of the exemplary device, a specific gas is capable of being produced from each of a multiplicity of liquid sources, solvent or oil based, e.g., by transporting gas bubbles through an array or forest of nanoscale or microscale subdivided paths to induce many subdivided microbubbles and increase the overall surface area of the bubbles (by a factor of at least 3, preferably at least 6, and even more preferably at least 12 for increased diffusion of scent molecules from a given volume of solvent or oil to the bubbles.

In some examples of the exemplary device, a scented gas can be produced by transporting gas through an array or forest of nanoscale or microscale subdivided paths within a highly porous structure fed and replenished from a scent-containing solvent or oil source.

In some examples of the exemplary gas-generating devices, the subdividing structure can be selected from large-surface-area nano/microwires, nano/micro ribbons, nano/micropores, aggregate of nano/microparticles, or aggregate of nano/micro capsules, with these structures being either vertically aligned, randomly or optimally distributed.

In some examples of the exemplary gas-generating devices, the subdividing structure of the large-surface-area nano/microwires, nano/micro ribbons, nano/micropores, aggregate of nano/microparticles, or aggregate of nano/micro capsules can be immersed in a scent-generating liquid and the bubbling of air or gas collects one of more of the selected scents and transports them.

In some examples of the exemplary gas-generating devices, the subdividing structure of the large-surface-area nano/microwires, nano/micro ribbons, nano/micropores, aggregate of nano/microparticles, or aggregate of nano/micro capsules, can be essentially dry, and not immersed in a bulk liquid of scent-generating material, and no air or gas bubbles are present, with the large-surface-area nano/microwires, nano/micro ribbons, nano/micropores, aggregate of nano/microparticles, or aggregate of nano/micro capsules, already comprised of previously soaked scent-generating liquid or are continuously or continually supplied with scent-generating liquid, either occasionally or periodically, so as to induce adsorbed, absorbed or soaked material on or in the large-surface-area nano/micro structures.

In some examples of the exemplary gas-generating devices, the adsorbed, absorbed or soaked scent-generating liquid can be supplied to the large-surface-area nano/microstructures to hold the scent-generating composition (in liquid, dried or semi-dried solid form) in or on the nano/microstructures, utilizing methods including without limitation burst fluxing with scent-generating liquid, short-time vigorous bubbling, capillary suction from the reservoir of the scent-generating liquid, intermittent supply of the scent-generating liquid through internal or sideway channels in the large-surface-area nano/microstructures using short-time air flow or vacuum suction, or via a wicking mechanism/structure set up to transfer scent-generating liquid from a liquid reservoir (internal or external) to the large-surface area nano/micro structure.

In some examples of the exemplary gas-generating devices, the subdividing structure can also serve as a local electrical or wireless heater to enhance bubble formation and diffusion of scent molecules from the solvent or oil to the bubbles, or to enhance release of scent molecules from the adsorbed, absorbed or soaked scent-generating liquid on or in the large-surface-area nano/micro structures.

In some examples of the exemplary gas-generating devices, the transport of the gas through guided delivery paths can be accelerated by an individual microfan dedicated to each path or by a single shared fan positioned near or at the exit region of the device.

In some examples, the disclosed technology includes methods for various processes of fabricating or assembling the devices and materials of the disclosed devices and systems as described in the drawings and in the specification.

In some examples, the exemplary gas-generating and releasing devices can be used for consumer, industrial, civilian or military applications, e.g., including, but not limited to, entertainment such as motion pictures, videogames, live shows, exhibitions and theater; fashion; clothing; communications; retailing; advertising; as an air freshener; perfumery; sensory/multisensory enhancement or effect; medical therapeutics, drug delivery or virtual surgery; education; training; testing; diagnostics; sampling; olfactory branding; olfactory displays; food, flavor or taste enhancement or modulation; health; sports enhancement, simulation or training; malodor control or masking; as an insect or animal repellent or attractant; pet or animal care; hygiene; aromatherapy; biofeedback; detoxification; and/or behavioral influence or control.

In some examples, the exemplary gas-generating and releasing devices can be configured as standalone, position-fixed, handheld, portable and/or wearable devices or equipment to be potentially incorporated into or within, used in conjunction with or attached as an accessory or peripheral to the following examples: clothing, furniture, furnishings or fixtures; accessories such as jewelry, watches, helmets, music headphones, augmented reality eyewear and normal eyeglasses; vehicles; mobile phones, computers; laptops, notebooks, notepads, electronic or physical books; training or diagnostic equipment; packaging of any kind; consumer goods; gift and greeting cards; medical equipment; military equipment; magazines; videogame consoles, iPods, radios, televisions and other broadcast or media-playable equipment.

In some examples, the exemplary devices can be triggered to activate/deactivate by non-wireless or wireless means, and capable of being synchronized to the workings or content delivery, transmission, transfer or broadcast of any other device, equipment or media.

In some examples, the exemplary scent generating devices can include the synchronization of the scent release timing with the exact moment for the corresponding screen or otherwise displayed image, voicemail, written, audio or audiovisual message, presentation, transmission or broadcast, and other control and powering device components, optionally combined with various memory technologies or devices, audio, visual or audiovisual technologies or devices and other sensory technologies and devices (haptics, etc). The coding mechanism to synchronize the image (or other virtual or augmented reality actions employing, for example, sound, music, mechanical vibration, 3D or other projection techniques, etc.) with the corresponding scent release can be based on image recognition, voice recognition, electronic timing recognition, motion, color and/or light sensors, as well as by utilizing hidden image, sound, electronic or wireless signals from images displayed that can be recognized/detected by the scent-releasing device to initiate or stop release of specific scent(s).

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A scent delivery device, comprising:
 a cartridge structured to include one or more chambers containing one or more scented substances;
 a housing structured to include a compartment to hold the cartridge, an opening to allow the one or more scented substances to dispense to an outer environment from the device, and one or more transporting channels formed between the compartment and the opening, wherein each of the one or more transporting channels is configured to deliver a scented substance from the corresponding chamber to the opening for delivering a scent from the one or more scented substances; and
 an actuator switch arranged in a corresponding transporting channel and operable to move between an open position and a closed position based on an applied signal to selectively allow passage of the scented substance from the corresponding transporting channel, wherein the actuator switch includes magnetically latchable gating structures including a first and a second mating magnetic components that are coupled in the closed position and uncoupled in the open position, wherein the first mating magnetic component includes a solenoid formed of a solenoid core having a substantially square-loop magnetization loop material, and wherein the second mating magnetic component is structured to bend or change its translational position upon a change in magnetic field from the solenoid core to actuate the opening or closing of the actuator switch in the transporting channel.

2. The device as in claim 1, wherein each scented substance includes a gas, vapor, or liquid.

3. The device as in claim 1, wherein the actuator switch is operable by actuation of a magnetic, piezoelectric, or thermal actuation mechanism.

4. The device as in claim 1, wherein the applied signal includes a pulsed electrical current having a pulse duration of less than 1 second.

5. The device as in claim 4, wherein the open position or the closed position of the actuator switch is maintained without any use of additional electrical power after the pulsed electrical current is applied.

6. The device as in claim 1, wherein the applied signal includes a pulsed magnetic field having a pulse duration of less than 1 second.

7. The device as in claim 6, wherein the applied pulsed magnetic field is produced by an applied multiple cycle electrical current.

8. The device as in claim 7, wherein the electrical current and the resultant magnetic field is generated with a gradually diminishing amplitude for demagnetization, whereby the actuator switch is actuated to move to the open position or the closed position without any additional electrical power after the multiple cycle electrical current is applied.

9. The device as in claim 1, wherein the solenoid core having the substantially square-loop magnetization loop material includes a remanent induction to magnetic saturation squareness ratio of at least 0.85.

10. The device as in claim 1, wherein the solenoid core having the substantially square-loop magnetization loop material provides a coercive force in a range of 20 Oe to 100 Oe.

11. The device as in claim 1, wherein one or both of the first and the second mating magnetic components includes a magnetic alloy including at least one of a square loop Fe—Cr—Co based spinodally decomposed alloy, a Fe—Cr base alloy, a Fe—Ni base alloy, a Fe—Cr—Ni base alloy, a Fe—Co base alloy, a Fe—Mo alloy, a Fe—Ni—Mo base alloy, a Fe—Si base alloy, a Cu—Ni—Fe based spinodally decomposed alloy, or a Cu—Ni—Co based spinodally decomposed alloy.

12. The device as in claim 11, wherein at least one of the square loop Fe—Cr—Co based spinodally decomposed alloy, the Fe—Cr base alloy, the Fe—Ni base alloy, the Fe—Cr—Ni base alloy, the Fe—Co base alloy, the Fe—Mo alloy, the Fe—Ni—Mo base alloy, or the Fe—Si base alloy includes at least 50 weight percent Fe.

13. The device as in claim 11, wherein at least one of the Cu—Ni—Fe based spinodally decomposed alloy, or the Cu—Ni—Co based spinodally decomposed alloy includes at least 50 weight percent Cu.

14. The device as in claim 1, wherein the first mating magnetic component is positioned vertically or horizontally in the transporting channel, and the second mating magnetic component includes a tip coated with a compliant elastometic material to form a tight sealing between the first and the second mating magnetic components when the actuator switch is in the closed position.

15. The device as in claim 1, further comprising:
an electrical circuit including an array of one or both of transistors and relay switches coupled to the actuator switches to control application of the applied signal to each of the actuator switches.

16. The device as in claim 1, wherein the one or more transporting channels are configured in an array of transporting nanoscale or microscale channels connecting the corresponding chambers to an array of openings of the housing.

17. The device as in claim 1, wherein the device dispenses a specific gas produced using a plurality of the fluids including scent-generating liquids, solvents or oil based fluids,
wherein the specific gas is produced by forming gas bubbles from the fluids and transporting the gas bubbles through an array of nanoscale or microscale channels to induce microbubbles with increased overall surface area than that of the gas bubbles.

18. The device as in claim 17, wherein the increased overall surface area is increased by a factor of at least 3.

19. The device as in claim 17, further comprising:
a scent-modifying structure formed of a highly porous material contained in one or both of the chamber of the cartridge or in the transporting channel the of the housing,
wherein the highly porous structure includes at least one of nanoscale or microscale wire structures, nanoscale or microscale ribbon structures, nanoscale or microscale structures with nanopores or micropores, nanoscale or microscale particles, or nanoscale or microscale capsules, and
wherein the gas bubbles are formed by passing air through the scent-modifying structure.

20. The device as in claim 19, wherein the air passed through the scent-modifying structure includes cold air having a temperature below 20° C., warm air having a temperature of 20° C. to 40° C., or hot air having a temperature between 40° C. and 70° C.

21. The device as in claim 19, wherein the nanoscale or microscale structures, particles, or capsules are configured to be vertically aligned or randomly aligned or distributed.

22. The device as in claim 19, wherein the nanoscale or microscale structures, particles, or capsules are immersed in the scented fluid.

23. The device as in claim 19, wherein the nanoscale or microscale structures, particles, or capsules are dry and previously immersed in the scented fluid.

24. The device as in claim 19, wherein the scent-generating liquid is supplied to the nanoscale or microscale structures, particles, or capsules of the highly porous structure by one or more of burst fluxing the scent-generating liquid, vigorous bubbling the scent-generating liquid, capillary suction of the scent-generating liquid, intermittent air flow or vacuum suction of the scent-generating liquid, or implementing a wicking mechanism.

25. The device as in claim 19, wherein the scent-modifying structure is operable as a local electrical or wireless heater to enhance bubble formation and diffusion of scent molecules from the liquid solvent or oil to form the gas bubbles, or to enhance release of the scent molecules from the scent-generating liquid on the nanoscale or microscale structures, particles, or capsules.

26. The device as in claim 1, further comprising:
one or more microscale fans configured in at least some of the corresponding one or more transporting channels to accelerate flow of the scented substance.

27. The device as in claim 1, wherein the cartridge is configured as a disposable, re-fillable, or replaceable cartridge.

28. The device as in claim 1, wherein the device is configured to be one of a handheld device, a wearable device, or a fixed device attached to a building, vehicle, or furniture.

29. The device as in claim 28, wherein the outer environment includes a space around the head of the user wearing the wearable device.

30. The device as in claim 1, wherein the device is configured for pre-programmed or timed release and dispensing of the scented substance.

31. The device as in claim 1, further comprising one or more scent diffusers coupled to the opening of the housing to control a diffusion or spreading of a scent from the one or more scented substances.

32. The device as in claim 31, wherein a scent diffuser is configured to have a porous geometry, channeled or wire-array geometry, spiral array, or gas blocking or reflecting geometry.

33. A scent delivery device, comprising:
a cartridge structured to include one or more chambers containing one or more scented substances;
a housing structured to include a compartment to hold the cartridge, an opening to allow the one or more scented substances to dispense to an outer environment from the device, and one or more transporting channels formed between the compartment and the opening, wherein each of the one or more transporting channels is configured to deliver a scented substance from the corresponding chamber to the opening for delivering a scent from the one or more scented substances; and
an actuator switch arranged in a corresponding transporting channel and operable to move between an open position and a closed position based on an applied signal to selectively allow passage of the scented substance from the corresponding transporting channel, wherein the actuator switch includes:
a plug formed in the transporting channel and including an orifice to allow the scented substance to flow, and
a spring component configured in the transporting channel proximate the orifice of the plug and operable to move toward and away from the orifice based on the applied signal causing the spring component to thermally expand to block the orifice or retract to not block the orifice.

34. The device as in claim 33, wherein the spring component is formed of a thermally expandable material.

35. The device as in claim 34, wherein the applied signal includes an electrical current through the spring component to cause resistive heating of the spring component to thermally expand and block the orifice.

36. The device as in claim 33, wherein the plug is formed of a compliant elastomeric material.

37. A scent delivery device, comprising:
a cartridge structured to include one or more chambers containing one or more scented substances;
a housing structured to include a compartment to hold the cartridge, an opening to allow the one or more scented substances to dispense to an outer environment from the device, and one or more transporting channels formed between the compartment and the opening, wherein each of the one or more transporting channels is configured to deliver a scented substance from the corresponding chamber to the opening for delivering a scent from the one or more scented substances; and
an actuator switch arranged in a corresponding transporting channel and operable to move between an open position and a closed position based on an applied signal to selectively allow passage of the scented substance from the corresponding transporting channel, wherein the actuator switch includes:
a plug formed in the transporting channel and including an orifice to allow the scented substance to flow, and
a piezoelectric component configured in the transporting channel proximate the orifice of the plug and operable to move toward and away from the orifice based on the applied signal causing the piezoelectric component to expand to block the orifice or retract to not block the orifice.

38. The device as in claim 37, wherein the applied signal includes an electrical voltage applied to the piezoelectric component to cause a piezoelectric effect in the piezoelectric component to expand or retract.

39. The device as in claim 37, wherein the plug includes a compliant elastomeric material.

* * * * *